(12) United States Patent
Whalley et al.

(10) Patent No.: US 10,799,467 B2
(45) Date of Patent: *Oct. 13, 2020

(54) USE OF THE PHYTOCANNABINOID CANNABIDIVARIN (CBDV) IN THE TREATMENT OF EPILEPSY

(71) Applicants: GW Pharma Limited, Salisbury (GB); Otsuka Pharmaceutical Co., Limited, Tokyo (JP)

(72) Inventors: Ben Whalley, Reading (GB); Claire Williams, Reading (GB); Gary Stephens, Reading (GB); Takashi Futamura, Osaka (JP)

(73) Assignees: GW Pharma Limited, Wiltshire (GB); Otsuka Pharmaceutical Co. Limited, Tokyo (JP)

( * ) Notice: Subject to any disclaimer, the term of this patent is extended or adjusted under 35 U.S.C. 154(b) by 92 days.

This patent is subject to a terminal disclaimer.

(21) Appl. No.: 14/685,753

(22) Filed: Apr. 14, 2015

(65) Prior Publication Data

US 2015/0320698 A1    Nov. 12, 2015

Related U.S. Application Data

(63) Continuation of application No. 13/075,873, filed on Mar. 30, 2011, now Pat. No. 9,125,859.

(30) Foreign Application Priority Data

Mar. 30, 2010 (GB) .................................. 1005364.3
Jan. 4, 2011 (GB) .................................. 1100042.9

(51) Int. Cl.
| | | |
|---|---|---|
| *A61K 31/05* | (2006.01) | |
| *A61K 31/515* | (2006.01) | |
| *A61K 31/19* | (2006.01) | |
| *A61K 31/352* | (2006.01) | |
| *A61K 31/40* | (2006.01) | |
| *A61K 36/185* | (2006.01) | |
| *A61K 45/06* | (2006.01) | |

(52) U.S. Cl.
CPC .............. *A61K 31/05* (2013.01); *A61K 31/19* (2013.01); *A61K 31/352* (2013.01); *A61K 31/40* (2013.01); *A61K 31/515* (2013.01); *A61K 36/185* (2013.01); *A61K 45/06* (2013.01)

(58) Field of Classification Search
CPC ...... A61K 31/05; A61K 31/19; A61K 31/352; A61K 31/40; A61K 31/515; A61K 36/185; A61K 45/06
See application file for complete search history.

(56) References Cited

U.S. PATENT DOCUMENTS

| | | |
|---|---|---|
| 6,403,126 B1 | 6/2002 | Webster |
| 6,949,582 B1 | 9/2005 | Wallace |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,125,859 B2 * | 9/2015 | Whalley ............... A61K 31/05 |
| 9,168,278 B2 | 10/2015 | Guy et al. |
| 9,474,726 B2 | 10/2016 | Guy et al. |
| 9,522,123 B2 | 12/2016 | Whalley et al. |
| 2006/0039959 A1 | 2/2006 | Wessling |
| 2008/0119544 A1 | 5/2008 | Guy et al. |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0270845 A1 | 10/2012 | Bannister et al. |
| 2013/0245110 A1 | 9/2013 | Guy et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2015/0181924 A1 | 7/2015 | Llamas |
| 2015/0335590 A1 | 11/2015 | Whalley et al. |
| 2015/0359755 A1 | 12/2015 | Guy et al. |
| 2015/0359756 A1 | 12/2015 | Guy et al. |
| 2016/0166514 A1 | 6/2016 | Guy et al. |
| 2016/0166515 A1 | 6/2016 | Guy et al. |

(Continued)

FOREIGN PATENT DOCUMENTS

| | | |
|---|---|---|
| GB | 2 384 707 A | 8/2003 |
| GB | 2 434 097 A | 7/2007 |
| GB | 2 434 312 A | 7/2007 |

(Continued)

OTHER PUBLICATIONS

Eggers Medical Hypothesis, 2007, 69, 1284-1289.*
Klitgaard et al. Seizure, 2003, 12:92-100.*
Third Party Observations for Application No. EP11712658.1 dated Nov. 22, 2013.
Statement of Opposition for EP10734541.5 mailed Dec. 5, 2014.
Combined Search and Examination Report dated Mar. 25, 2011 for Application No. GB1100043.7.
Examination Report dated Mar. 18, 2014 for Application No. GB1100043.7.

(Continued)

*Primary Examiner* — Kara R McMillian
(74) *Attorney, Agent, or Firm* — Finnegan, Henderson, Farabow, Garrett & Dunner, LLP

(57) ABSTRACT

This invention relates to the use of the phytocannabinoid cannabidivarin (CBDV) and combinations of the phytocannabinoid CBDV with tetrahydrocannabivarin (THCV) and cannabidiol (CBD) in the treatment of epilepsy. The invention further relates to the use of the phytocannabinoid CBDV in combination with standard anti-epileptic drugs (SAEDs). Preferably the SAED is one of ethosuximide, valproate or phenobarbital.

6 Claims, 25 Drawing Sheets

(56) References Cited

U.S. PATENT DOCUMENTS

| | | | |
|---|---|---|---|
| 2016/0220529 | A1 | 8/2016 | Guy et al. |
| 2017/0007551 | A1 | 1/2017 | Guy et al. |

FOREIGN PATENT DOCUMENTS

| | | | |
|---|---|---|---|
| GB | 2 450 753 A | 1/2009 | |
| GB | 2 456 183 A | 7/2009 | |
| GB | 2 471 523 A | 1/2011 | |
| GB | 2 478 595 A | 9/2011 | |
| GB | 2 479 153 A | 10/2011 | |
| GB | 2 485 291 A | 5/2012 | |
| GB | 2 471 565 B | 7/2012 | |
| GB | 2 478 072 B | 12/2012 | |
| GB | 2 478 074 B | 12/2012 | |
| GB | 2 492 487 A | 1/2013 | |
| WO | WO 02/064109 A2 | 8/2002 | |
| WO | WO 03/099302 A1 | 12/2003 | |
| WO | WO 04/016246 A1 | 2/2004 | |
| WO | WO 04/016277 A2 | 2/2004 | |
| WO | WO 2006/054057 A2 | 5/2006 | |
| WO | WO 2006/133941 A2 | 12/2006 | |
| WO | WO 2007/083098 A1 | 7/2007 | |
| WO | WO 2007/138322 A1 | 12/2007 | |
| WO | WO 2008/094181 A2 | 8/2008 | |
| WO | WO 2008/129258 A1 | 10/2008 | |
| WO | WO 2008/146006 A1 | 12/2008 | |
| WO | WO 2009/007697 A1 | 1/2009 | |
| WO | WO 2011/001169 A1 | 1/2011 | |
| WO | WO 2011/121351 A1 | 10/2011 | |
| WO | WO 2012/093255 A1 | 7/2012 | |
| WO | WO 2013/032351 A1 | 3/2013 | |
| WO | WO 2013/045891 A1 | 4/2013 | |
| WO | WO 2015/142501 A1 | 9/2015 | |
| WO | WO 2015/184127 A2 | 12/2015 | |
| WO | WO 2015/193667 A1 | 12/2015 | |
| WO | WO 2015/193668 A1 | 12/2015 | |
| WO | WO 2016/059404 A1 | 4/2016 | |

OTHER PUBLICATIONS

Combined Search and Examination Report dated Jan. 4, 2012 for Application No. GB1116789.7.
Examination Report dated Feb. 29, 2012 for Application No. GB1121919.3.
Combined Search and Examination Report dated Sep. 5, 2014 for Application No. GB1414813.4.
International Search Report and Written Opinion dated Dec. 13, 2010 for Application No. PCT/GB2010/051066.
International Preliminary Report on Patentability dated Jun. 9, 2011 for Application No. PCT/GB2010/051066.
International Search Report and Written Opinion dated May 30, 2011 for Application No. PCT/GB2011/050649.
International Search Report dated Feb. 24, 2012 for Application No. PCT/GB2012/050002.
International Search Report and Written Opinion dated Nov. 16, 2012 for Application No. PCT/GB2012/052284.
International Preliminary Report on Patentability dated Dec. 12, 2013 for Application No. PCT/GB2012/052284.
[No Author Listed] Estimating the Maximum Safe Starting Dose in Initial Clinical Trials for Therapeutics in Adult Healthy Volunteers. FDA Guidance for Industry, Jul. 2005.
Alger, Not too excited? Thank your endocannabinoids. Neuron. Aug. 17, 2006;51(4):393-5.
Ames et al., Anticonvulsant effect of cannabidiol. S Afr Med J. Jan. 4, 1986;69(1):14.
Arain et al., Pregabalin in the management of partial epilepsy. Neuropsychiatr Dis Treat. 2009;5:407-13. Epub Aug. 20, 2009.
Avoli et al., Cellular and molecular mechanisms of epilepsy in the human brain. Prog Neurobiol. Oct. 2005;77(3):166-200.
Bancaud et al., Proposal for Revised Clinical and Electroencephalographic Classification of Epileptic Seizures. Epilepsia. Aug. 1981;22(4):489-501.
Bhatt et al., Indigenous plants in traditional healthcare system in Kedarnath valley of western Himalaya. Indian J Tradit Knowl. Apr. 2008;7(2):300-10.
Bhattacharyya et al., Modulation of mediotemporal and ventrostriatal function in humans by Delta9-tetrahydrocannabinol: a neural basis for the effects of Cannabis sativa on learning and psychosis. Arch Gen Psychiatry. Apr. 2009;66(4):442-51. doi:10.1001/archgenpsychiatry.2009.17.
Bostanci et al., The effects of octanol on penicillin induced epileptiform activity in rats: an in vivo study. Epilepsy Res. Oct. 2006;71(2-3):188-94. Epub Jul. 27, 2006.
Brust et al., Marijuana use and the risk of new onset seizures. Trans Am Clin Climatol Assoc. 1992;103:176-81.
Carlini et al., Hypnotic and antiepileptic effects of cannabidiol. J Clin Pharmacol. Aug.-Sep. 1981;21(8-9 Suppl):417S-427S. Medline abstract only.
Consroe et al., Anticonvulsant interaction of cannabidiol and ethosuximide in rats. J Pharm Pharmacol. Aug. 1977;29(8):500-1.
Consroe et al., Anticonvulsant nature of marihuana smoking. JAMA. Oct. 20, 1975;234(3):306-7.
Consroe et al., Cannabidiol—antiepileptic drug comparisons and interactions in experimentally induced seizures in rats. J Pharmacol Exp Ther. Apr. 1977;201(1):26-32.
Consroe et al., Effects of cannabidiol on behavioral seizures caused by convulsant drugs or current in mice. Eur J Pharmacol. Sep. 24, 1982;83(3-4):293-8.
Cortesi et al., Potential therapeutical effects of cannabidiol in children with pharmacoresistant epilepsy. Med Hypotheses. 2007;68(4):920-1. Epub Nov. 16, 2006.
Cunha et al., Chronic administration of cannabidiol to healthy volunteers and epileptic patients. Pharmacology. 1980;21(3):175-85.
Czapinski et al., Randomized 36-month comparative study of valproic acid (VPA), phenytoin (PHT), phenobarbital (PB) and carbamazepine (CBZ) efficacy in patients with newly diagnosed epilepsy with partial complex seizures. J Neurolog Sci. Sep. 1997;150:S162. Abstract only. 2 pages.
Davis et al., A predominant role for inhibition of the adenylate cyclase/protein kinase a pathway in ERK activation by cannabinoid receptor 1 in N1E-115 neuroblastoma cells. J Biol Chem. Dec. 5, 2003;278(49):48973-80. Epub Sep. 29, 2003.
Davis et al., Antiepileptic action of marijuana-active substances. Federation Proceedings. 1949;8:284-5.
Deshpande et al., Cannabinoid CB1 receptor antagonists cause status epilepticus-like activity in the hippocampal neuronal culture model of acquired epilepsy. Neurosci Lett. Jan. 2007;411(1):11-6. Epub Nov. 15, 2006.
Engel, Report of the ILAE classification core group. Epilepsia. Sep. 2006;47(9):1558-68.
Ferdinand et al., Cannabis—psychosis pathway independent of other types of psychopathology. Schizophr Res. Nov. 15, 2005;79(2-3):289-95. Epub Aug. 25, 2005.
Fisher et al., The impact of epilepsy from the patient's perspective I. Descriptions and subjective perceptions. Epilepsy Res. Aug. 2000;41(1):39-51.
Gabor et al., Lorazepam versus phenobarbital : Candidates for drug of choice for treatment of status epilepticus. J Epilepsy. Jan. 1990;3(1):3-6.
Gastaut, Clinical and electroencephalographical classification of epileptic seizures. Epilepsia. Mar. 1970;11(1):102-13.
Gross et al., Marijuana use and epilepsy: prevalence in patients of a tertiary care epilepsy center. Neurology. Jun. 8, 2004;62(11):2095-7.
Hill et al., $\Delta^9$-Tetrahydrocannabivarin suppresses in vitro epileptiform and in vivo seizure activity in adult rats. Epilepsia. Aug. 2010;51(8):1522-32. doi: 10.1111/j.1528-1167.2010.02523.x. Epub Feb. 26, 2010.
Iuvone et al., Neuroprotective effect of cannabidiol, a non-psychoactive component from Cannabis sativa, on beta-amyloid-induced toxicity in PC12 cells. J Neurochem. Apr. 2004;89(1):134-41.
Jeavons et al., Sodium valproate in treatment of epilepsy. Br Med J. Jun. 15, 1974;2(5919):584-6.

(56) References Cited

OTHER PUBLICATIONS

Jones et al., Cannabidiol displays antiepileptiform and antiseizure properties in vitro and in vivo. J Pharmacol Exp Ther. Feb. 2010;332(2):569-77. doi: 10.1124/jpet.109.159145. Epub Nov. 11, 2009.
Joy et al., Marijuana and Medicine. Assessing the Science Base. National Academy Press. Washington D.C. 1999. 170 pages.
Karler et al., The cannabinoids as potential antiepileptics. J Clin Pharmacol. Aug.-Sep. 1981;21(8-9 Suppl):437S-447S.
Khan et al., Khazaain-al-Advia, vol. I. 1911: 889. Urdu. Exhibit 3.
Khan et al., Khazaain-al-Advia, vol. I. 1911: 889. Urdu. Exhibit 4.
Khan et al., Muheet-e-Azam, vol. II. 1887: 147. Persian. Exhibit 1.
Long et al., The pharmacological actions of cannabidiol. Drugs of the Future. Jul. 2005;30(7):747-53.
Lutz, On-demand activation of the endocannabinoid system in the control of neuronal excitability and epileptiform seizures. Biochem Pharmacol. Nov. 1, 2004;68(9):1691-8.
Mackie, Cannabinoid receptors as therapeutic targets. Annu Rev Pharmacol Toxicol. 2006;46:101-22.
Majoosi, et al. Kaamil-al-Sena'ah, Part II, Central Council for Research in Unani Medicine. 2005:116. Arabic. Exhibit 2.
McCormick et al., On the cellular and network bases of epileptic seizures. Annu Rev Physiol. 2001;63:815-46.
Merlis, Proposal for an international classification of the epilepsies. Epilepsia. Mar. 1970;11(1):114-9.
Ng et al., Illicit drug use and the risk of new-onset seizures. Am J Epidemiol. Jul. 1990;132(1):47-57.
Obay et al., Antiepileptic effects of ghrelin on pentylenetetrazole-induced seizures in rats. Peptides. Jun. 2007;28(6):1214-9. Epub Apr. 19, 2007.
Pereira et al., Study pharmacologic of the GABAergic and glutamatergic drugs on seizures and status epilepticus induced by pilocarpine in adult Wistar rats. Neurosci Lett. Jun. 4, 2007;419(3):253-7. Epub Apr. 13, 2007.
Pertwee, Cannabinoid receptor ligands: clinical and neuropharmacological considerations, relevant to future drug discovery and development. Expert Opin Investig Drugs. Jul. 2000;9(7):1553-71.
Pohl et al., Effects of flunarizine on Metrazol-induced seizures in developing rats. Epilepsy Res. Sep. 1987;1(5):302-5.
Rauca et al., The role of superoxide dismutase and alpha-tocopherol in the development of seizures and kindling induced by pentylenetetrazol-influence of the radical scavenger alpha-phenyl-N-tert-butyl nitrone. Brain Res. May 29, 2004;1009(1-2):203-12.
Resstel et al., 5-HT1A receptors are involved in the cannabidiol-induced attenuation of behavioural and cardiovascular responses to acute restraint stress in rats. Br J Pharmacol. Jan. 2009;156(1):181-8.
Sander, The epidemiology of epilepsy revisited. Curr Opin Neurol. Apr. 2003;16(2):165-70.
Scuderi et al., Cannabidiol in medicine: a review of its therapeutic potential in CNS disorders. Phytother Res. May 2009;23(5):597-602.
Swann et al., The effects of seizures on the connectivity and circuitry of the developing brain. Ment Retard Dev Disabil Res Rev. 2004;10(2):96-100.
Thomas et al., Evidence that the plant cannabinoid Delta9-tetrahydrocannabivarin is a cannabinoid CB1 and CB2 receptor antagonist. Br J Pharmacol. Dec. 2005;146(7):917-26.
Trembly et al., Double-blind clinical study of cannabidiol as a secondary anticonvulsant. Marijuana '90 International Conference on Cannabis and Cannabinoids. Kolymbari, Crete. Jul. 8-11, 1990.
Usami et al., Synthesis and pharmacological evaluation in mice of halogenated cannabidiol derivatives. Chem Pharm Bull (Tokyo). Nov. 1999;47(11):1641-5.
Vollner et al., Haschisch XX: Cannabidivarin, ein neuer Haschisch-Inhaltsstoff. Tetrahedron Lett. 1969;10(3):145-7.
Wahle et al., Development of tolerance to the anticonvulsant effect of valproate but not to ethosuximide in a rat model of absence epilepsy. Eur J Pharma. May 1990;181(1-2):1-8.
Wallace et al., Assessment of the role of CB1 receptors in cannabinoid anticonvulsant effects. Eur J Pharmacol. Sep. 28, 2001;428(1):51-7.
Weston et al., Tetrahydrocannabivarin exhibits anticonvulsant effects in a piriform cortical brain slice model of epileptiform activity. Pro British Pharm Soc 75th Anniv Meeting. Dec. 31, 2006 Found on: http://www.pA2online.org/abstract/abstract.jsp?abid=28533. Abstract Only. 1 Page.
Wingerchuk, Cannabis for medical purposes: cultivating science, weeding out the fiction. Lancet. Jul. 24-30, 2004;364(9431):315-6.
Yuriev, Endogenic cannabinoid system is a new perspective object of pharmacotherapeutic effect to disease of nervous system, Ukrainsky Metodichny Chasopis, 2005; 6(50): 21-9.
Zuardi et al., Cannabidiol, a Cannabis sativa constituent, as an antipsychotic drug. Braz J Med Biol Res. Apr. 2006;39(4):421-9. Epub Apr. 3, 2006.
[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.
[No Author Listed] Cannabinoid. Wikipedia. Retrieved on Jul. 9, 2015 from https://en.wikipedia.org/wiki/Cannabinoid.
[No Author Listed] GW Pharmaceuticals Announces Epidiolex Receives Fast Track Designation from FDA for the Treatment of Dravet Syndrome. GW Pharmaceuticals Press Release dated Jun. 6, 2014.
[No Author Listed] GW Pharmaceuticals Announces Physician Reports of Epidiolex Treatment Effect in Children and Young Adults with Treatment-resistant epilepsy from Physician-Led Expanded Access Treatment Program. GW Pharmaceuticals Press Release dated Jun. 17, 2014.
Consroe et al., Anticonvulsant drug antagonism of delta9tetrahydrocannabinol-induced seizures in rabbits. Res Commun Chem Pathol Pharmacol. Jan. 1977;16(1):1-13.
Dravet, The core Dravet syndrome phenotype. Epilepsia. Apr. 2011;52 Suppl 2:3-9. doi: 10.1111/j.1528-1167.2011.02994.x.
Eadie, Shortcomings in the current treatment of epilepsy. Expert Rev Neurother. Dec. 2012;12(12):1419-27. doi: 10.1586/ern.12.129.
Gresham et al., Treating Lennox-Gastaut syndrome in epileptic pediatric patients with third-generation rufinamide. Neuropsychiatr Dis Treat. Oct. 5, 2010;6:639-45. doi: 10.2147/NDT.S6465.
Kramer et al., Febrile infection-related epilepsy syndrome (FIRES): pathogenesis, treatment, and outcome: a multicenter study on 77 children. Epilepsia. Nov. 2011;52(11):1956-65. doi:10.1111/j.1528-1167.2011.03250.x. Epub Aug. 29, 2011.
Kwan et al., Definition of drug resistant epilepsy: consensus proposal by the ad hoc Task Force of the ILAE Commission on Therapeutic Strategies. Epilepsia. Jun. 2010;51(6):1069-77. doi:10.1111/j.1528-1167.2009.02397.x. Epub Nov. 3, 2009. Erratum in: Epilepsia. Sep. 2010;51(9):1922.
Maa et al., The case for medical marijuana in epilepsy. Epilepsia. Jun. 2014;55(6):783-6. doi: 10.1111/epi.12610. Epub May 22, 2014.
Mechoulam et al., Toward drugs derived from cannabis. Naturwissenschaften. Apr. 1978;65(4):174-9.
Porter et al., Report of a parent survey of cannabidiol-enriched cannabis use in pediatric treatment-resistant epilepsy. Epilepsy Behav. Dec. 2013;29(3):574-7. doi: 10.1016/j.yebeh.2013.08.037.
Press et al., Parental reporting of response to oral cannabis extracts for treatment of refractory epilepsy. Epilepsy Behav. Apr. 2015;45:49-52. doi: 10.1016/j.yebeh.2015.02.043. Epub Apr. 3, 2015.
Stott et al., Cannabinoids for the pharmaceutical industry. Euphytica. 2004;140:83-93.
Thurman et al., Standards for epidemiologic studies and surveillance of epilepsy. Epilepsia. Sep. 2011;52 Suppl 7:2-26. doi:10.1111/j.1528-1167.2011.03121.x.
[No Author Listed] GW Pharmaceuticals Provides Update on Orphan Program in Childhood Epilepsy for Epidiolex. GW Pharmaceuticals press release dated Nov. 15, 2013.

(56) References Cited

OTHER PUBLICATIONS

[No Author Listed] GW Pharmaceuticals Receives Orphan Drug Designation by FDA for Epidiolex® in the Treatment of Lennox-Gastaut Syndrome. GW Pharmaceuticals press release dated Feb. 28, 2014.

[No Author Listed] Salutaris Drops Buy Salutaris Drops—Salutaris Drops. Oct. 12, 2014. Last accessed from http://web.archive.org/web/20141012130255/http://salutarisdrops.com/buy-salutaris-drops/ on Jan. 20, 2017.

[No Author Listed] Salutaris Drops Cannabidiol for Aicardi Syndrome—Salutaris Drops. Oct. 12, 2014. Last accessed from http://web.archive.org/web/20141012220050/http://salutarisdrops.com/cannabidiol-aicardi-syndrome/ on Jan. 20, 2017.

Booth, Legalization's opening of medical pot research is dream and nightmare. The Denver Post. Dec. 14, 2013. Last accessed from http://www.denverpost.com/2013/12/14/legalizations-opening-of-medical-pot-research-is-dream-and-nightmare/ on Jan. 20, 2017.

Gardner, Comes Now Epidiolex. Oct. 23, 2013. Last accessed from http://theava.com/archives/24412 on Jan. 20, 2017.

Geffrey et al., Cannabidiol (CBD) Treatment for Refractory Epilepsy in Tuberous Sclerosis Complex (TSC). American Epilepsy Society. 2014: Abstract 2.427. Last accessed from https://www.aesnet.org/meetings_events/annual_meeting_abstracts/view/1868979 on Jun. 30, 2015.

Gloss et al., Cannabinoids for epilepsy. Cochrane Database Syst Rev. Mar. 5, 2014;(3):CD009270. doi: 10.1002/14651858.CD009270.pub3.

Jacobson et al., Survey of Current Cannabidiol Use in Pediatric Treatment-Resistant Epilepsy. Apr. 22, 2013. Last Accessed from http://www.thcint.com/uploads/1/9/3/7/19371199/cannabidiol_use_in_pediatric_epilepsy.pdf on Jan. 20, 2017.

Pelliccia et al., Treatment with CBD in oily solution of drug-resistant paediatric epilepsies. 2005 Congress of Cannabis and the Cannabinoids. Leiden, The Netherlands: International Association for Cannabis as Medicine. p. 14.

Hill et al., Cannabidivarin-rich cannabis extracts are anticonvulsant in mouse and rat via a CB1 receptor-independent mechanism. Br J Pharmacol. Oct. 2013;170(3):679-92. doi:10.1111/bph.12321.

Rosenthaler et al., Differences in receptor binding affinity of several phytocannabinoids do not explain their effects on neural cell cultures. Neurotoxicol Teratol. Nov.-Dec. 2014;46:49-56. doi: 10.1016/j.ntt.2014.09.003. Epub Oct. 12, 2014. Erratum in: Neurotoxicol Teratol. Mar.-Apr. 2016;54( ):89-93.

* cited by examiner

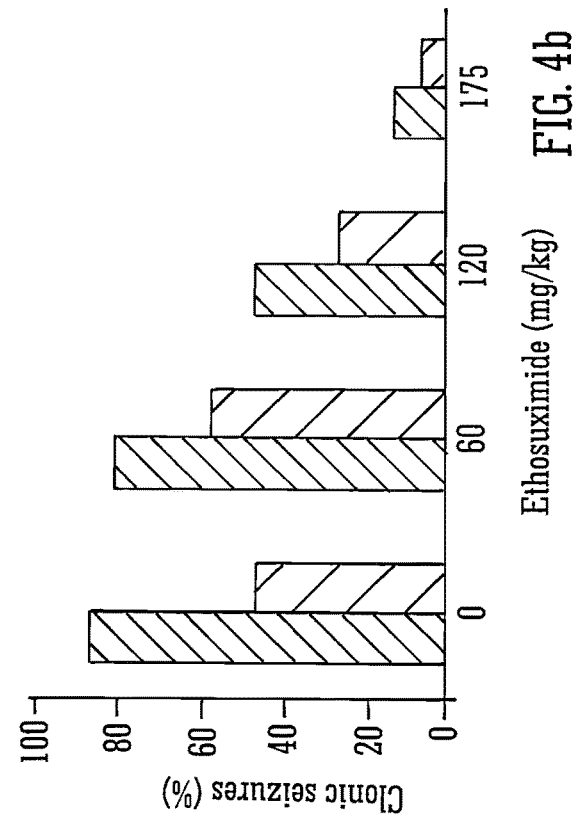
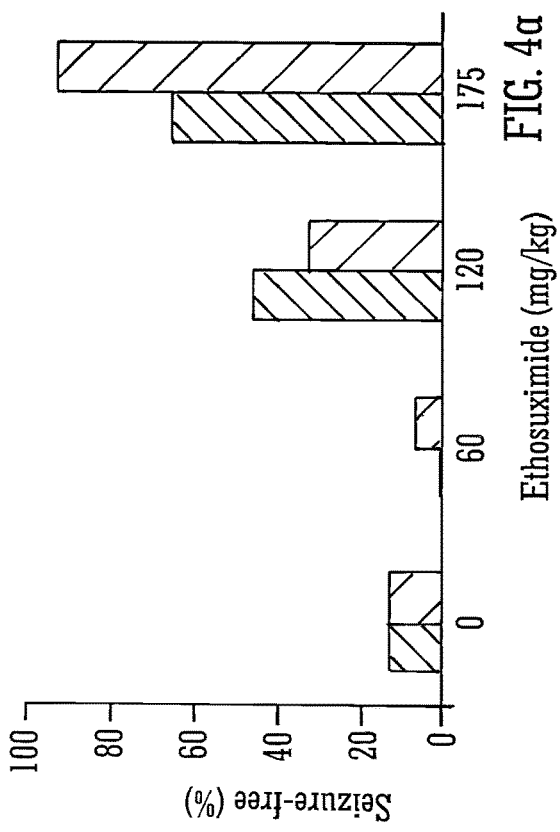
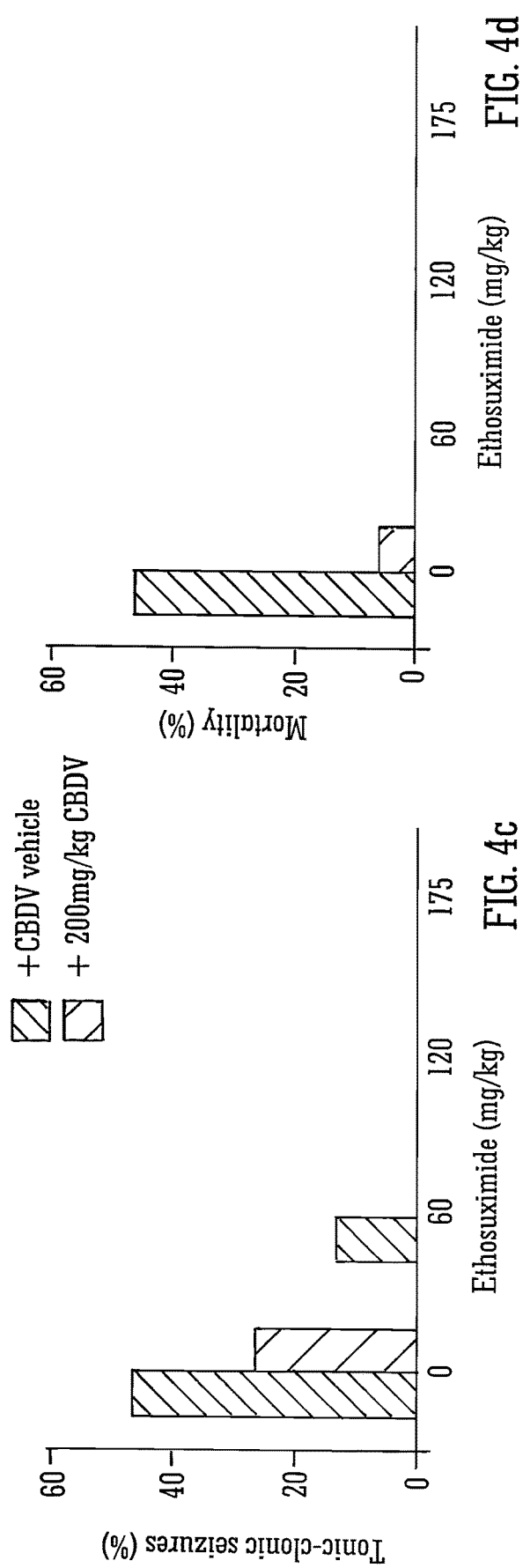
FIG. 4a
FIG. 4b
FIG. 4c
FIG. 4d

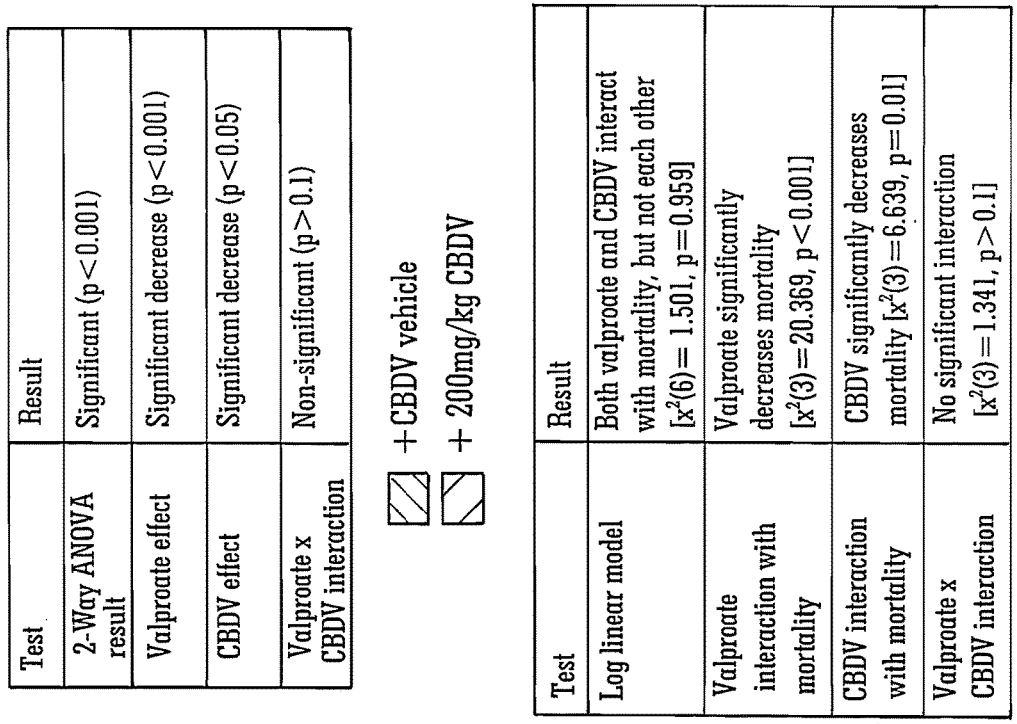
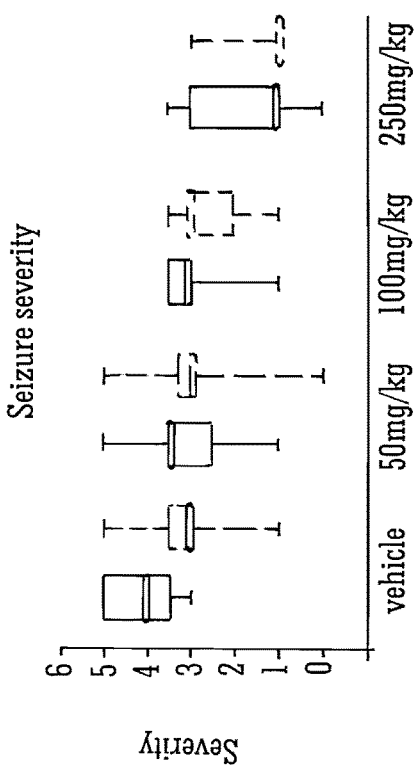
FIG. 6a
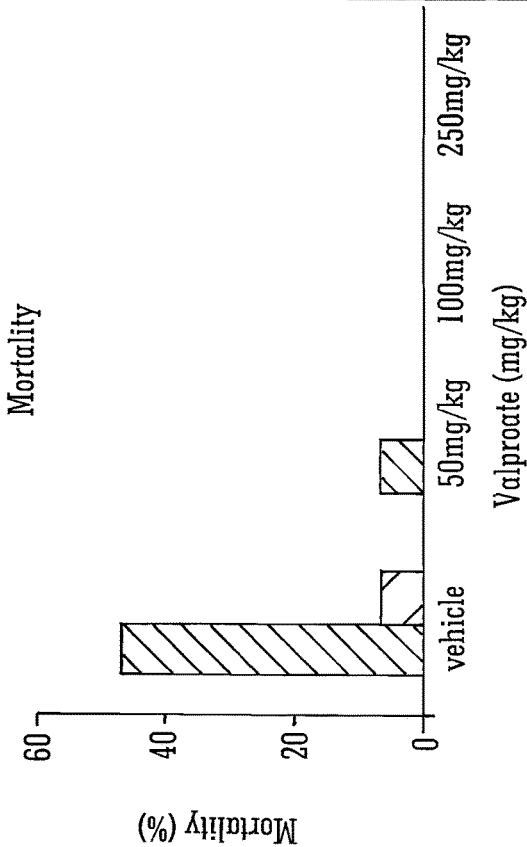
FIG. 6b

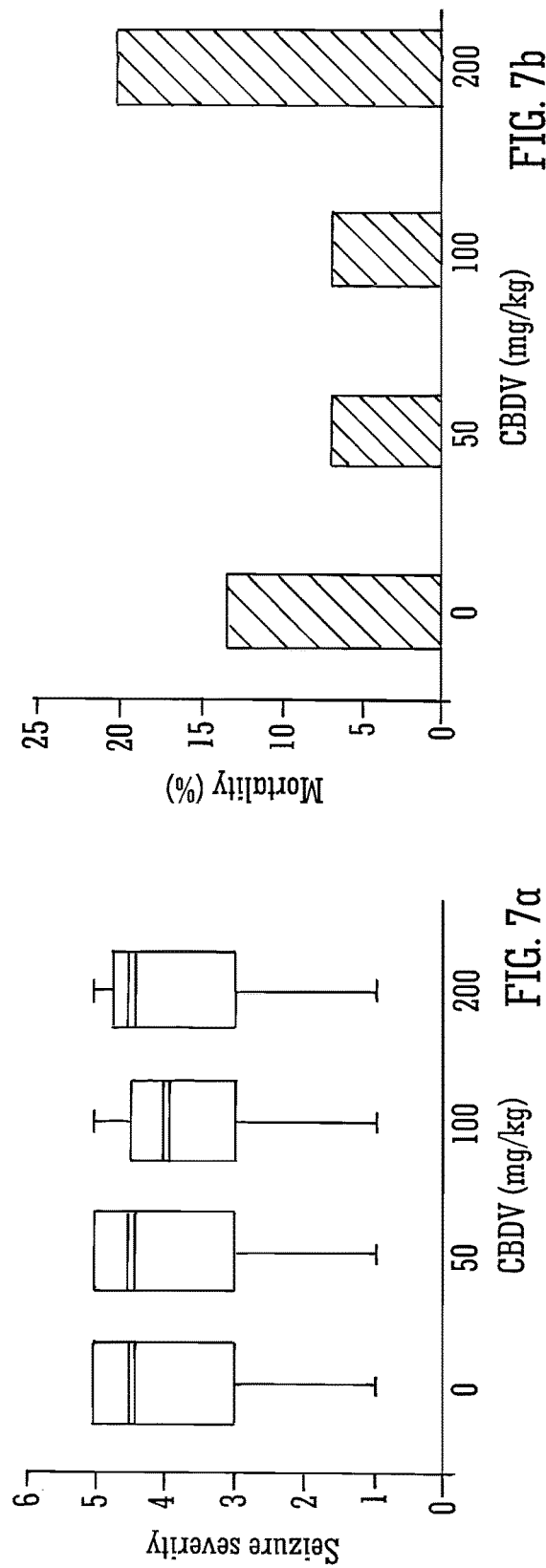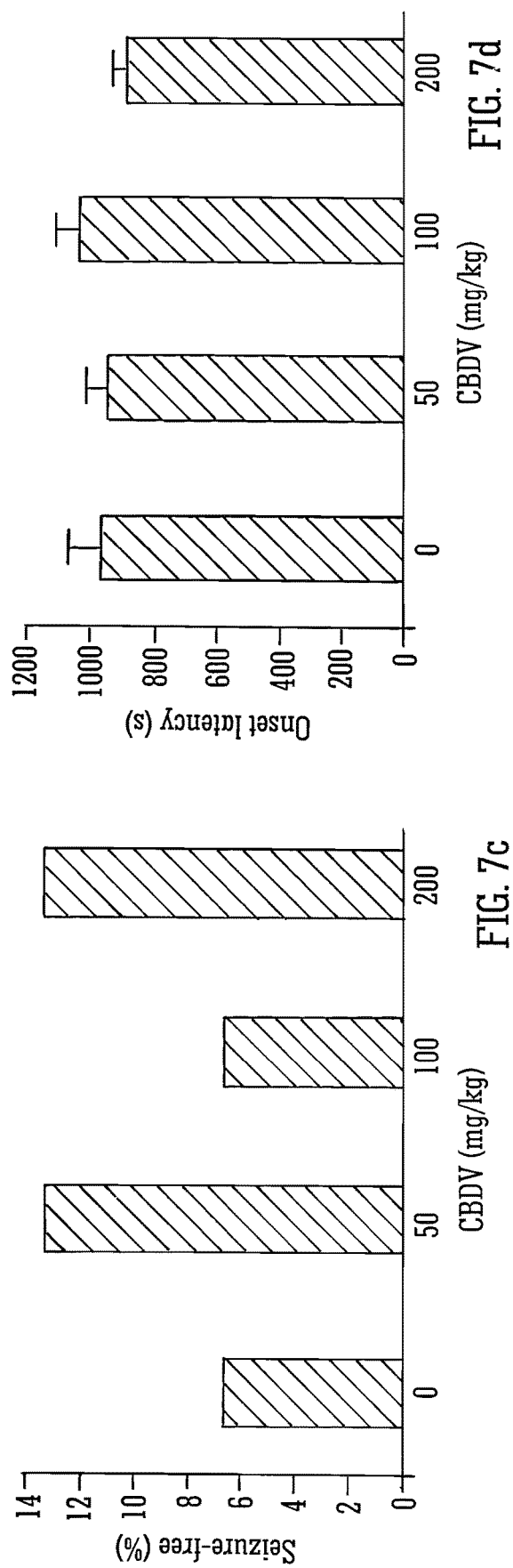

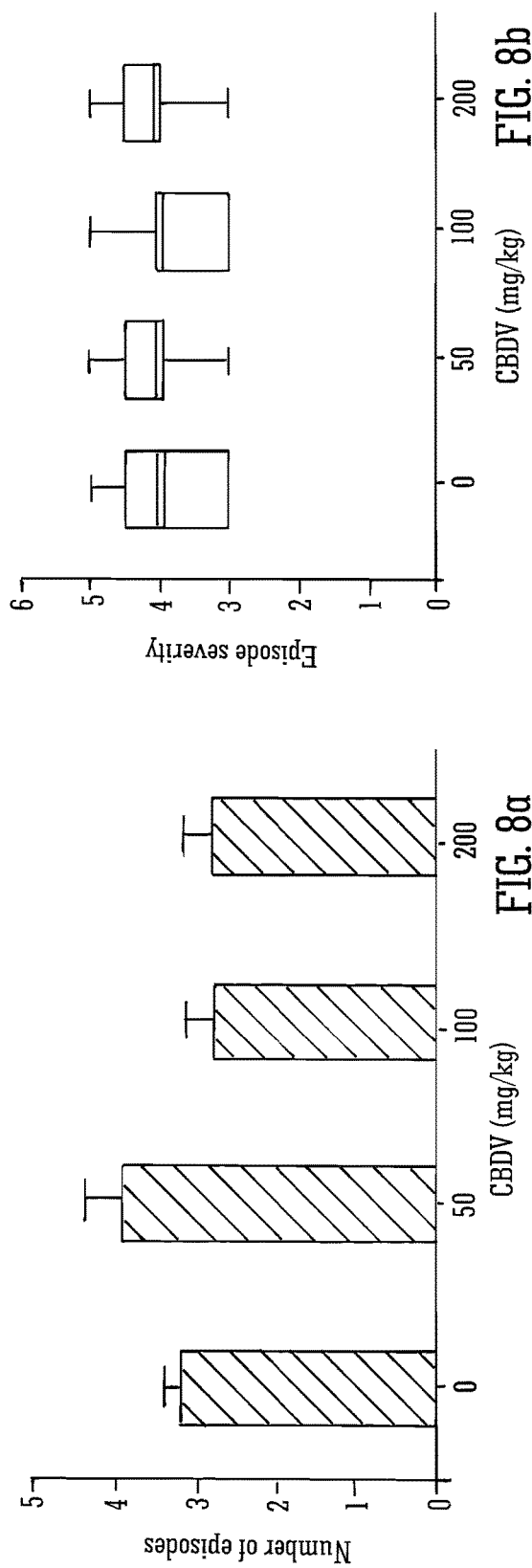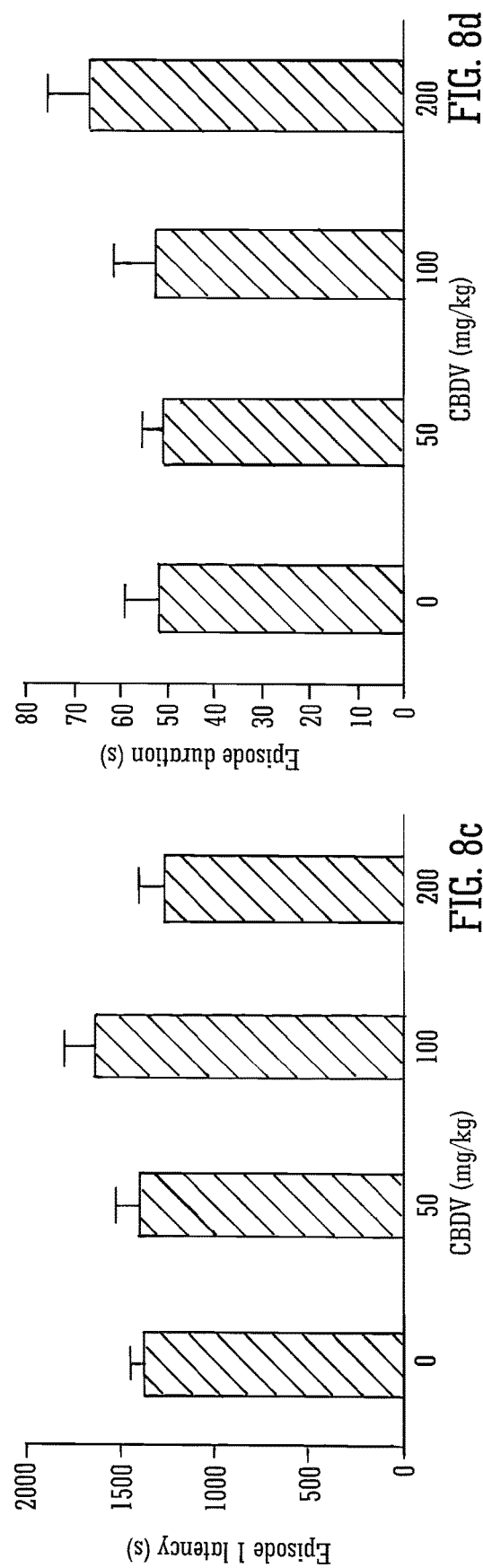
FIG. 8a FIG. 8b FIG. 8c FIG. 8d

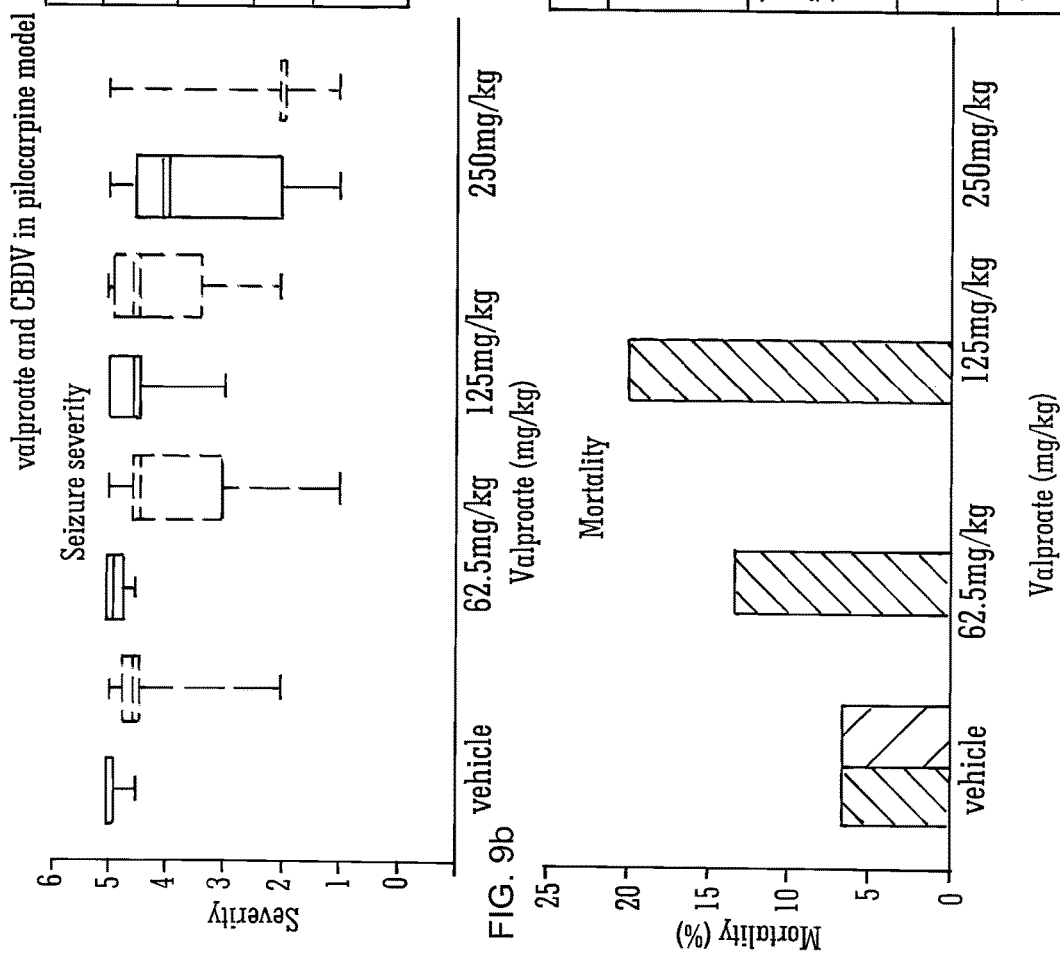

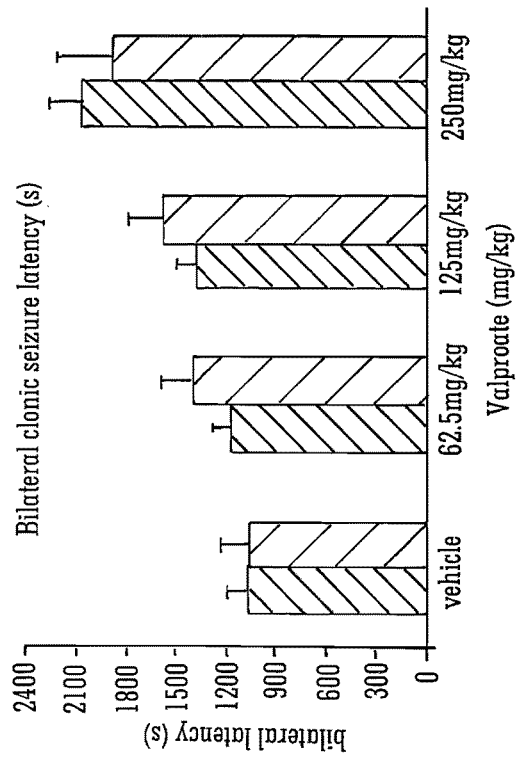# 
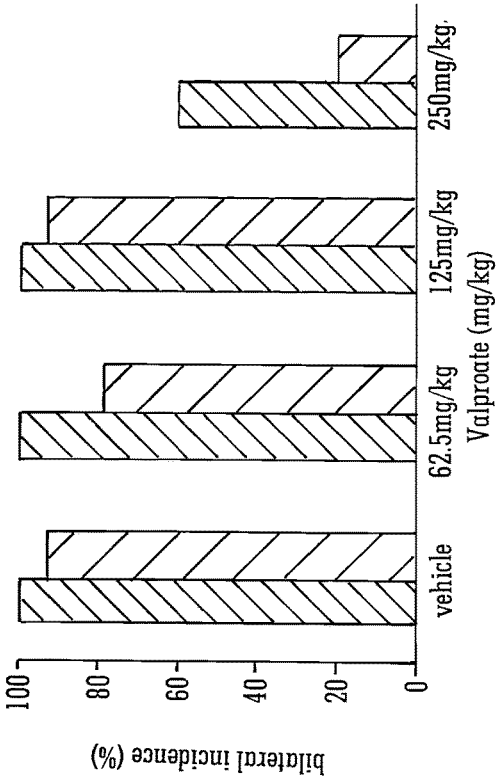
FIG. 10a
FIG. 10b

USE OF THE PHYTOCANNABINOID CANNABIDIVARIN (CBDV) IN THE TREATMENT OF EPILEPSY

RELATED APPLICATIONS

This application is a continuation of U.S. patent application Ser. No. 13/075,873, filed Mar. 30, 2011, the entire contents of which are incorporated herein by reference.

FIELD OF THE INVENTION

This invention relates to the use of the phytocannabinoid cannabidivarin (CBDV) and combinations of the phytocannabinoid CBDV with tetrahydrocannabivarin (THCV) and cannabidiol (CBD) in the treatment of epilepsy. The invention further relates to the use of the phytocannabinoid CBDV in combination with standard anti-epileptic drugs (SAEDs). Preferably the CBDV is used in combination with a SAED with a mechanism of action which acts via sodium or calcium channels, more preferably one which:
- modifies low-threshold or transient neuronal calcium currents, as exemplified by ethosuximide; or
- reduces high-frequency neuronal firing and sodium-dependent action potentials and may additionally enhance GABA effects, as exemplified by valproate.

Alternatively the CBDV is used in combination with a SAED with a mechanism of action which:
- enhances GABAergic inhibition, as exemplified by phenobarbital.

BACKGROUND

Epilepsy is a chronic neurological disorder presenting a wide spectrum of diseases that affects approximately 50 million people worldwide (Sander, 2003). Advances in the understanding of the body's internal 'endocannabinoid' system has lead to the suggestion that cannabis-based medicines may have the potential to treat this disorder of hyperexcitability in the central nervous system (Mackie, 2006, Wingerchuk, 2004, Alger, 2006).

*Cannabis* has been ascribed both pro-convulsant (Brust et al., 1992) and anti-convulsant effects. Therefore, it remains to determine whether cannabinoids represent a yet to be unmasked therapeutic anticonvulsant or, conversely, a potential risk factor to recreational and medicinal users of cannabis (Ferdinand et al., 2005).

In 1975 Consroe et al. described the case of young man whose standard treatment (phenobarbital and phenytoin), didn't control his seizures. When he began to smoke cannabis socially he had no seizures. However when he took only cannabis the seizures returned. They concluded that 'marihuana may possess an anti-convulsant effect in human epilepsy'.

A study by Ng (1990) involved a larger population of 308 epileptic patients who had been admitted to hospital after their first seizure. They were compared to a control population of 294 patients who had not had seizures, and it was found that using cannabis seemed to reduce the likelihood of having a seizure. However this study was criticized in an Institute of Medicine report (1999) which claimed it was 'weak', as 'the study did not include measures of health status prior to hospital admissions and differences in their health status might have influenced their drug use' rather than the other way round.

Three controlled trials have investigated the anti-epilepsy potential of cannabidiol. In each, cannabidiol was given in oral form to sufferers of generalised grand mal or focal seizures.

Cunha et al (1980) reported a study on 16 grand mal patients who were not doing well on conventional medication. They received their regular medication and either 200-300 mg of cannabidiol or a placebo. Of the patients who received CBD, 3 showed complete improvement, 2 partial, 2 minor, while 1 remained unchanged. The only unwanted effect was mild sedation. Of the patients who received the placebo, 1 improved and 7 remained unchanged.

Ames (1986) reported a less successful study in which 12 epileptic patients were given 200-300 mg of cannabidiol per day, in addition to standard antiepileptic drugs. There seemed to be no significant improvement in seizure frequency.

Trembly et al (1990 performed an open trial with a single patient who was given 900-1200 mg of cannabidiol a day for 10 months. Seizure frequency was markedly reduced in this single patient.

In addition to the disclosures suggesting CBD may be beneficial there is a report (Davis & Ramsey) of tetrahydrocannabinol (THC) being administered to 5 institutionalized children who were not responding to their standard treatment (phenobarbital and phenoytin). One became entirely free of seizures, one became almost completely free of seizures, and the other three did no worse than before.

In WO 2006/054057 it is suggested that the cannabinoid Tetrahydrocannabivarin (THCV) may behave as anti epileptic, something confirmed by Thomas et al 2005.

The application WO 2007/138322 shows CBD to be an inverse agonists at the CB1 and CB2 receptors and suggests this compound and structurally related compounds including CBDV, may have a therapeutic benefit in a wide range of conditions which involve these receptors. More specifically the data demonstrates that the cannabinoid CBD reduced bodyweight in rats.

However other work on cannabinoids has shown that despite THCV's structural similarity to THC the two compounds behave quite differently at the CB1 receptor and consequently it does not follow that the propyl cannabinoid analogs will behave as their pentyl equivalents.

In addition a study in 2007 by Deshpande et al. established that the CB1 antagonist rimonabant was a pro-convulsant; this study demonstrated that antagonism of the CB1 receptor caused epileptic activity. The inference from this study is that cannabinoids which act as antagonists of the CB1 receptor may not be useful as anti-convulsants; indeed they may exacerbate such a condition.

WO 2009/007697 describes a THCV and CBD pharmaceutical formulation. Such a formulation is suggested to be of use in many different types of diseases including epilepsy.

The application WO 2007/083098 describes the use of cannabis plant extracts with neuroprotective properties. Cannabinoid extracts containing THC and CBD were shown to be more effective than their pure counterparts in this area of medicine.

The application WO 02/064109 describes a pharmaceutical formulation where the cannabinoids THC and CBD are used. The application goes on to state that the propyl analogs of these cannabinoids may also be used in the formulation. Since this application was written it has been shown that THCV behaves in a very different manner to THC and therefore the assumption that the propyl analogs of cannabinoids may behave in a similar manner to their pentyl counterparts is now not valid.

The application GB0911580.9 describes the use of THCV for the treatment of generalised seizures, and also describes the use of CBD in combination with THCV.

However, there are more than forty recognisable types of epileptic syndrome partly due to seizure susceptibility varying from patient to patient (McCormick and Contreras, 2001, Lutz, 2004) and a challenge is finding drugs effective against these differing types.

Neuronal activity is a prerequisite for proper brain function. However, disturbing the excitatory-inhibitory equilibrium of neuronal activity may induce epileptic seizures. These epileptic seizures can be grouped into two basic categories:
a) partial, and
b) generalised seizures.

Partial seizures originate in specific brain regions and remain localised—most commonly the temporal lobes (containing the hippocampus), whereas generalised seizures appear in the entire forebrain as a secondary generalisation of a partial seizure (McCormick and Contreras, 2001, Lutz, 2004). This concept of partial and generalised seizure classification did not become common practice until the International League Against Epilepsy published a classification scheme of epileptic seizures in 1969 (Merlis, 1970, Gastaut, 1970, Dreifuss et al., 1981).

The International League Against Epilepsy further classified partial seizures, separating them into simple and complex, depending on the presence or the impairment of a consciousness state (Dreifuss et al., 1981).

The league also categorized generalised seizures into numerous clinical seizure types, some examples of which are outlined below:

Absence seizures occur frequently, having a sudden onset and interruption of ongoing activities. Additionally, speech is slowed or impeded with seizures lasting only a few seconds (Dreifuss et al., 1981).

Tonic-clonic seizures, often known as "grand mal", are the most frequently encountered of the generalised seizures (Dreifuss et al., 1981). This generalised seizure type has two stages: tonic muscle contractions which then give way to a clonic stage of convulsive movements. The patient remains unconscious throughout the seizure and for a variable period of time afterwards.

Atonic seizures, known as "drop attacks", are the result of sudden loss of muscle tone to either a specific muscle, muscle group or all muscles in the body (Dreifuss et al., 1981).

The onset of epileptic seizures can be life threatening with sufferers also experiencing long-term health implications (Lutz, 2004). These implications may take many forms:
mental health problems (e.g. prevention of normal glutamatergic synapse development in childhood);
cognitive deficits (e.g. diminishing ability of neuronal circuits in the hippocampus to learn and store memories); and
morphological changes (e.g. selective loss of neurons in the CA1 and CA3 regions of the hippocampus in patients presenting mesial temporal lobe epilepsy as a result of excitotoxicity) (Swann, 2004, Avoli et al., 2005)

It is noteworthy that epilepsy also greatly affects the lifestyle of the sufferer—potentially living in fear of consequential injury (e.g. head injury) resulting from a grand mal seizure or the inability to perform daily tasks or the inability to drive a car unless having had a lengthy seizure-free period (Fisher et al., 2000).

Despite the historic work on CBD in epilepsy in the 1980's/1990's research in the field of anti-convulsants has focused on many other candidates many of which are now approved for use in the treatment of epilepsy. Such drugs include: acetozolamide, carbamazepine, clobazam, clonazepam, ethosuximide, eslicarbazepine acetate, gabapentin, lacosamide, lamotriquine, levetiracetam, oxcarbazepine, Phenobarbital, phenytoin, pregabalin, primidone, rufinamide, sodium valproate, tiagabine, topiramate, valproate, vigabatrin, and zonisamide.

The mode of action of some of these is understood and for others is unknown. Some modes of action are set out in Table 1 below: (Adapted from: Schachter S C. Treatment of seizures. In: Schachter S C, Schomer D L, eds. The comprehensive evaluation and treatment of epilepsy. San Diego, Calif.: Academic Press; 1997. p. 61-74)

TABLE 1

| Antiepileptic drug | Mechanism of action | Sodium or calcium or GABA channel involvement |
|---|---|---|
| Barbiturates: primidone (Mysoline), phenobarbital | Enhances GABAergic inhibition | GABA |
| Carbamazepine (Tegretol, Tegretol-XR, Carbatrol) | Inhibits voltage-dependent sodium channels | Sodium |
| Ethosuximide (Zarontin) | Modifies low-threshold or transient neuronal calcium currents | Calcium |
| Felbamate (Felbatol) | Unknown | |
| Gabapentin (Neurontin) | Unknown | |
| Lamotrigine (Lamictal) | Inhibits voltage-dependent sodium channels, resulting in decreased release of the excitatory neurotransmitters glutamate and aspartate | Sodium |
| Phenytoin (Dilantin, Phenytek) | Blocks sodium-dependent action potentials; reduces neuronal calcium uptake | Sodium/Calcium |
| Valproate (Depakote, Depakote ER, Depakene, valproic acid) | Reduces high-frequency neuronal firing and sodium-dependent action potentials; enhances GABA effects | Sodium/GABA |

However despite the introduction of some twenty different compounds for treatment of epilepsy over the last twenty years there remains a need for alternate drugs for several reasons:

i) 1-2% of the world's population suffer from epilepsy (http://www.ncbi.nlm.nih.gov/sites/ppmc/articles/PMC1808496/);
ii) Of these 30% are refractory to existing treatments; and
iii) There are also notable motor side effects in the existing therapies (http://en.wikipedia.org/wiki/Epilepsy).

For example valproate and ethosuximide both exhibit notable motor and other side effects (including sedation) when given to rats at doses greater than 200 mg/kg, as does phenobarbitone at doses greater than 250 mg/kg in rat models of epilepsy.

Three well-established and extensively used in vivo models of epilepsy are:
pentylenetetrazole-induced (PTZ) model of generalised seizures (Obay et al., 2007, Rauca et al., 2004);
pilocarpine-induced model of temporal lobe (i.e. hippocampus) seizures (Pereira et al., 2007); and
penicillin-induced model of partial seizures (Bostanci and Bagirici, 2006).

These provide a range of seizure and epilepsy models, essential for therapeutic research in humans.

SUMMARY OF THE INVENTION

It is an object of the present invention to identify novel anti-convulsants for use in the treatment of epilepsy.

Preferably the novel anti-convulsant will be effective in areas currently not adequately provided for by existing medications, standard anti-epileptic drugs (SAEDs).

Preferably the novel anti-convulsant will have a better side effect profile than existing SAEDs particularly when it comes to motor side effects.

Additionally is would be desirable for the compounds to work alongside standard treatments for epilepsy, addressing unmet needs and/or allowing lower dosages to be used thereby countering some of the adverse effects of such existing SAEDs.

According to one aspect of the invention, a formulation comprising CBDV and at least one pharmaceutically acceptable excipient.

According to another aspect of the invention, a method for the treatment of epileptic seizures is provided. The method comprises administering to a subject in need thereof a therapeutically effective amount of the phytocannabinoid CBDV. In some embodiments, the type of epileptic seizure to be treated is a generalised seizure or a temporal lobe seizure. The CBDV may be administered with one or more therapeutically effective phytocannabinoids. Examples of one or more therapeutically effective phytocannabinoids include, but are not limited to THCV and CBD. In some embodiments, the CBDV is administered with one or more therapeutically effective phytocannabinoids, wherein the one or more therapeutically effective phytocannabinoids are THCV and CBD.

In some embodiments, the CBDV is in an isolated form. In some embodiments, the CBDV is in the form of a botanical drug substance.

The CBDV may be used in combination with a standard anti-epileptic drug. Examples of standard anti-epileptic drug includes, but are not limited, standard anti-epileptic drug having a mechanism of action which acts via sodium or calcium channels, or enhances GABAergic inhibition. In some embodiments, the standard anti-epileptic drug is phenobarbital. In some embodiments, the standard anti-epileptic drug having a mechanism of action which acts via sodium or calcium channels either modifies low-threshold or transient neuronal calcium currents; or reduces high-frequency neuronal firing and sodium-dependent action potentials and may additionally enhance GABA effects. In some embodiments, the standard anti-epileptic drug is slected from the group comprising ethosuximide and valproate.

According to another aspect of the invention, a method for the treatment of epileptic seizures is provided. The method comprises administering to a subject in need thereof a therapeutically effective amount of a cannabis plant extract comprising a phytocannabinoid containing component and a non-phytocannabinoid containing component, wherein the phytocannabinoid containing component comprises at least 50% (w/w) of the cannabis plant extract and contains as a principal phytocannabinoid, CBDV and as a secondary phytocannabinoid, CBD, and wherein the non-phytocannabinoid containing component comprises a monoterpene fraction and a sesquiterpene fraction. In some embodiments, the method further comprises administering of THCV.

In some embodiments, the phytocannabinoid containing component comprises 64-78% (w/w) of the cannabis plant extract. In some embodiments, the phytocannabinoid containing component comprises 52-64% (w/w) CBDV of the total phytocannabinoid fraction. In some embodiments, the phytocannabinoid containing component comprises 22-27% (w/w) CBD of the total phytocannabinoid fraction. In some embodiments, the phytocannabinoid containing component comprises 3.9-4.7% (w/w) THCV of the total phytocannabinoid fraction.

Definitions

"Phytocannabinoids" are cannabinoids that originate from nature and can be found in the cannabis plant. The phytocannabinoids can be isolated cannabinoids or present as a botanical drug substance.

An "isolated cannabinoid" is defined as a phytocannabinoid that has been extracted from the cannabis plant and purified to such an extent that all the additional components such as secondary and minor cannabinoids and the non-cannabinoid fraction have been removed.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of cannabis, BDS derived from cannabis plants do not include highly purified Pharmacopoeial grade cannabinoids.

Preferably the components and the relative amounts thereof in the BDS are characterised to the extent that qualitatively at least 90% of the components are identified.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

The amount of phytocannabinoid-containing component in the BDS in some embodiments is greater than 55% (w/w), through 60%, 65%, 70%, 75%, 80% to 85% or more of the total extract. The actual amount is likely to depend on the starting material used and the method of extraction used.

The "principal phytocannabinoid" in a BDS is the phytocannabinoid that is present in an amount that is higher than that of the other phytocannabinoids. Preferably the principal phytocannabinoid is present in an amount greater than 40% (w/w) of the total extract. More preferably the principal phytocannabinoid is present in an amount greater than 50% (w/w) of the total extract. More preferably still the principal phytocannabinoid is present in an amount greater than 60% (w/w) of the total extract.

The amount of the principal phytocannabinoid in the BDS is preferably greater than 75% of the phytocannabinoid-containing fraction, more preferably still greater than 85% of the phytocannabinoid-containing fraction, and more preferably still greater than 95% of the phytocannabinoid-containing fraction.

In some cases, such as where the principal cannabinoid is either CBDV or THCVA the amount of the principal phytocannabinoid in the BDS is lower. Here the amount of phytocannabinoid is preferably greater than 55% of the phytocannabinoid-containing fraction.

The "secondary phytocannabinoid/s" in a BDS is the phytocannabinoid/s that is/are present in significant proportions. Preferably the secondary phytocannabinoid is present in an amount greater than 5% (w/w) of the total extract, more preferably greater than 10% (w/w) of the total extract, more preferably still greater than 15% (w/w) of the total extract. Some BDS's will have two or more secondary phytocannabinoids that are present in significant amounts. However not all BDS's will have a secondary phytocannabinoid. For example CBG BDS does not have a secondary phytocannabinoid in its extract.

The "minor phytocannabinoid/s" in a BDS can be described as the remainder of all the phytocannabinoid components once the principal and secondary phytocannabinoids are accounted for. Preferably the minor phytocannabinoids are present in total in an amount of less than 10% (w/w) of the total extract, more preferably still less than 5% (w/w) of the total extract, and most preferably the minor phytocannabinoid is present in an amount less than 2% (w/w) of the total extract.

Typically the non-phytocannabinoid containing component of the BDS comprises terpenes, sterols, triglycerides, alkanes, squalenes, tocopherols and carotenoids.

These compounds may play an important role in the pharmacology of the BDS either alone or in combination with the phytocannabinoid.

The "terpene fraction" may be of significance and can be broken down by the type of terpene: monoterpene or sesquiterpene. These terpene components can be further defined in a similar manner to the cannabinoids.

The amount of non-phytocannabinoid containing component in the BDS may be less than 45%, through 40%, 35%, 30%, 25%, 20% to 15% or less of the total extract. The actual amount is likely to depend on the starting material used and the method of extraction used.

The "principal monoterpene/s" in a BDS is the monoterpene that is present in an amount that is higher than that of the other monoterpenes. Preferably the principal monoterpene/s is present in an amount greater than 20% (w/w) of the total terpene content. More preferably the principal monoterpene is present in an amount greater than 30% (w/w) of the total terpene content, more preferably still greater than 40% (w/w) of the total terpene content, and more preferably still greater than 50% (w/w) of the total terpene content. The principal monoterpene is preferably a myrcene or pinene. In some cases there may be two principal monoterpenes. Where this is the case the principal monoterpenes are preferably a pinene and/or a myrcene.

The "principal sesquiterpene" in a BDS is the sesquiterpene that is present in an amount that is higher than all the other terpenes. Preferably the principal sesquiterpene is present in an amount greater than 20% (w/w) of the total terpene content, more preferably still greater than 30% (w/w) of the total terpene content. The principal sesquiterpene is preferably a caryophyllene and/or a humulene.

The sesquiterpene components may have a "secondary sesquiterpene". The secondary monoterpene is preferably a pinene, which is preferably present at an amount greater than 5% (w/w) of the total terpene content, more preferably the secondary terpene is present at an amount greater than 10% (w/w) of the total terpene content.

The secondary sesquiterpene is preferably a humulene which is preferably present at an amount greater than 5% (w/w) of the total terpene content, more preferably the secondary terpene is present at an amount greater than 10% (w/w) of the total terpene content.

Alternatively botanical extracts may be prepared by introducing isolated phytocannabinoids into a non-cannabinoid plant fraction as can be obtained from a zero cannabinoid plant or a CBG-free BDS.

The structure of CBDV is as shown below:

CBDV    Cannabidivarin

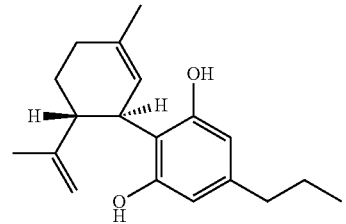 [SMILES: C=C(C)[C@@H]1CCC(C)=C[C@H]1c1c(O)cc(CCC)cc1O]

Phytocannabinoids can be found as either the neutral (decarboxylated form) or the carboxylic acid form depending on the method used to extract the cannabinoids. For example it is known that heating the carboxylic acid form will cause most of the carboxylic acid form to decarboxylate into the neutral form.

Phytocannabinoids can also occur as either the pentyl (5 carbon atoms) or propyl (3 carbon atoms) variant. Initially it was thought that the propyl and pentyl variants would have similar properties, however recent research suggests this is not true. For example the phytocannabinoid THC is known to be a CB1 receptor agonist whereas the propyl variant THCV has been discovered to be a CB1 receptor antagonist meaning that it has almost opposite effects.

This is confirmed by Pertwee (2000) in Cannabinoid receptor ligands: clinical and neuropharmacological considerations relevant to future drug discovery and development, which describes potential therapeutic targets for CB1 receptor antagonists which include appetite suppression, the reduction of L-dopa dyskinesia in patient's with Parkinson's disease, management of acute schizophrenia and the amelioration of cognitive memory dysfunctions associated with Alzheimer's disease. All of these therapeutic targets are very different from those suggested for CB1 receptor agonists such as appetite stimulation and reduction of pain.

A preferred CBDV formulation is one comprising CBDV BDS, isolated CBDV or synthetic CBDV in a form suitable for oral delivery. Forms suitable for oral delivery include capsules and tablets. In such formulations the active may be mixed with one or more excipients and may additionally comprise one or more SAEDs, although more typically combinations with SAEDs would be administered separately, sequentially or simultaneously.

Unit dosage amounts may vary depending on the type and severity of the epilepsy to be treated. Each dosage unit may comprise less than or equal to 1000 mg of CBDV and the number of doses to be taken may also be varied to suit a patient's requirements.

BRIEF SUMMARY OF THE DISCLOSURE

In accordance with a first aspect of the present invention there is provided a phytocannabinoid CBDV for use in the treatment of epileptic seizures.

Surprisingly in an MES model of epilepsy CBDV showed much greater anti-convulsant activity than CBD.

In accordance with a second aspect of the present invention there is provided the use of the phytocannabinoid CBDV in the manufacture of a medicament for use in the treatment of epileptic seizures.

The medicament may be a formulation comprising CBDV and at least one pharmaceutically acceptable excipient.

In accordance with a third aspect of the present invention there is provided a method for the treatment of epileptic seizures, which comprises administering to a subject in need thereof a therapeutically effective amount of the phytocannabinoid CBDV.

Preferably the type of epileptic seizure to be treated is a generalised seizure or a temporal lobe seizure.

In one embodiment the CBDV is used in combination with one or more therapeutically effective phytocannabinoids.

Preferably the one or more therapeutically effective phytocannabinoid is THCV and/or CBD.

In one embodiment the CBDV is in an isolated form.

In a further embodiment the CBDV is in the form of a botanical drug substance.

In a further embodiment still, the CBDV is used in combination with a standard anti-epileptic drug. The SAED may be one with a mechanism of action which acts via sodium or calcium channels, more preferably one which:

modifies low-threshold or transient neuronal calcium currents, as exemplified by ethosuximide; or reduces high-frequency neuronal firing and sodium-dependent action potentials and may additionally enhance GABA effects, as exemplified by valproate.

Alternatively the SAED may be one with a mechanism of action which enhances GABAergic inhibition, as exemplified by phenobarbital.

The combination (see Examples) demonstrates combinations can:

a. reduce the incidence of tonic-clonic seizures;
b. increase the amount of time a patient is seizure free;
c. increase the latency to onset of seizure;
d. decrease the overall duration of the seizure;
e. reduce the severity and mortality of the seizures; and
f. reduce the motor and other side effects (including sedation) associated with the SAEDs.

Thus, the combinations are particularly well suited in the treatment of conditions generally considered refractory to existing medication. The combinations would also appear to allow for the use of lower doses of the SAED's than would be used were the SAED to be used alone.

In accordance with a fourth aspect of the present invention there is provided a cannabis plant extract comprising a phytocannabinoid containing component and a non-phytocannabinoid containing component, wherein the phytocannabinoid containing component comprises at least 50% (w/w) of the cannabis plant extract and contains as a principal phytocannabinoid, CBDV, and as a secondary phytocannabinoid, CBD, and wherein the non-phytocannabinoid containing component comprises a monoterpene fraction and a sesquiterpene fraction, for use in the treatment of epileptic seizures.

In accordance with a fifth aspect of the present invention there is provided the use of a cannabis plant extract comprising a phytocannabinoid containing component and a non-phytocannabinoid containing component, wherein the phytocannabinoid containing component comprises at least 50% (w/w) of the cannabis plant extract and contains as a principal phytocannabinoid, CBDV, and as a secondary phytocannabinoid, CBD, and wherein the non-phytocannabinoid containing component comprises a monoterpene fraction and a sesquiterpene fraction, in the manufacture of a medicament for use in the treatment of epileptic seizures.

Preferably the cannabis plant extract further comprises THCV.

Preferably the phytocannabinoid containing component comprises 64-78% (w/w) of the cannabis plant extract.

Preferably the phytocannabinoid containing component comprises 52-64% (w/w) CBDV of the total phytocannabinoid fraction, 22-27% (w/w) CBD of the total phytocannabinoid fraction and 3.9-4.7% (w/w) THCV of the total phytocannabinoid fraction.

BRIEF DESCRIPTION OF THE DRAWINGS

Embodiments of the invention are further described hereinafter with reference to the accompanying drawings, in which

FIG. 4A-D shows the effect of CBDV and ethosuximide on incidence of seizures and mortality in PTZ-induced seizures;

FIG. 6A-B shows the effect of CBDV and valproate on seizure severity and mortality in PTZ-induced seizures;

FIG. 7A-D shows the effect of different doses of CBDV alone in Pilocarpine-induced seizures (seizure severity, mortality, seizure free and onset latency);

FIG. 8A-D shows the effect of different doses of CBDV on seizure episodes in Pilocarpine-induced seizures (number of episodes, episode severity, episode latency and episode duration);

FIG. 9A-B shows the effect of high dose (200 mg/Kg) CBDV and valproate in Pilocarpine-induced seizures (severity and mortality);

FIG. 10A-B shows the effect of high dose (200 mg/Kg) CBDV and valproate in Pilocarpine-induced seizures (bilateral latency and incidence);

Figure 1A:
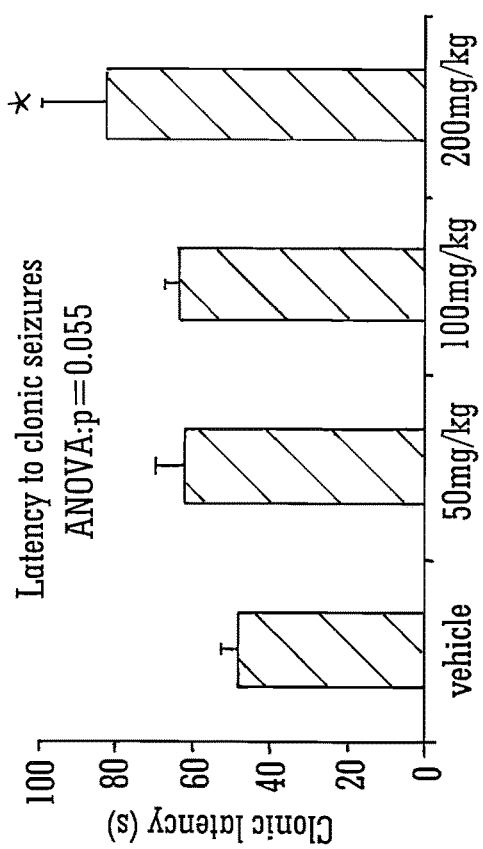
FIG. 1A-C shows the effect of CBDV on onset and development of PTZ-induced seizures.
Figure 1B:
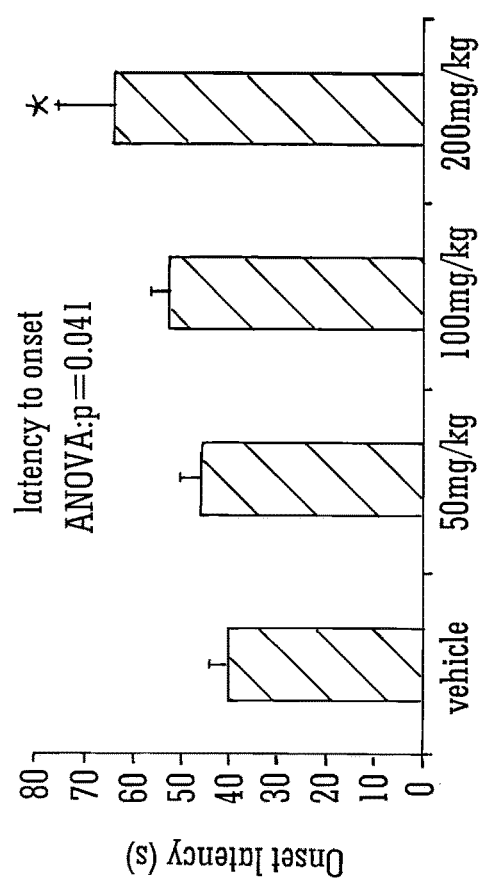
Figure 1C:
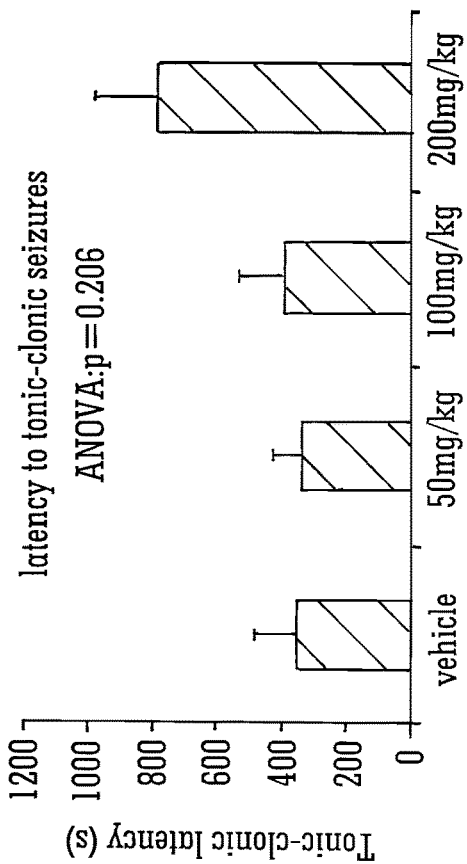

Legend to FIG. 1: A-C: mean latency to seizure onset (A), clonic (B) and tonic-clonic (C) seizures in s. Statistical significance was assessed by ANOVA and post hoc Tukey test, p≤0.05 was considered to be significant in both cases. Data is presented±S.E.M., * indicates p<0.05.

Legend to FIG. 2: A: Median severity of seizures (grey line), also shown is the $25^{th}$ and $75^{th}$ percentiles (black horizontal lines) and the maximum and minimum values (upward and downward error bars respectively). B: Proportion of animals in each group that developed tonic-clonic seizures. C: Proportion of animals in each group that died. D: Proportion of animals in each group that remained seizure free after PTZ administration. *,  and * indicate p≤0.05, 0.01 and 0.001 respectively. A: median data tested by ANOVA and post hoc Tukey's test. B-D: Percentages tested by binomial statistics test.

Figure 3B:
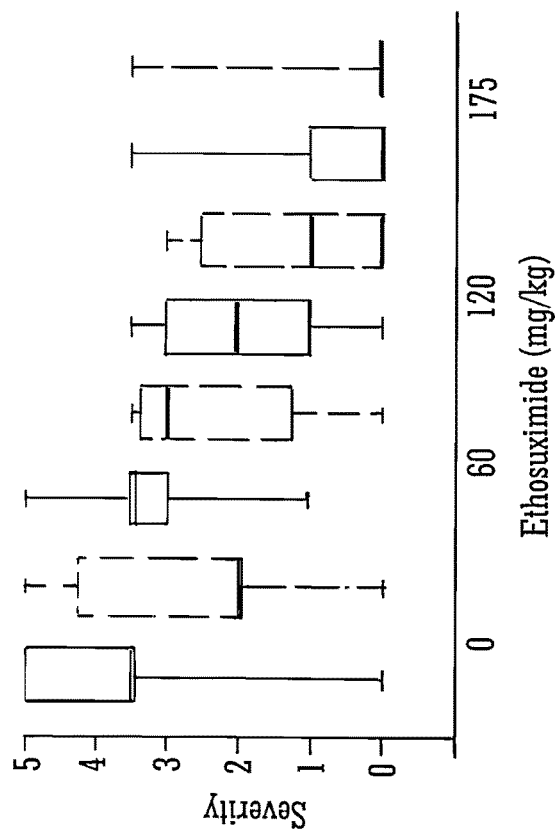
FIG. 3A-C shows the effect of CBDV and ethosuximide on PTZ-induced seizures.
Figure 3A:
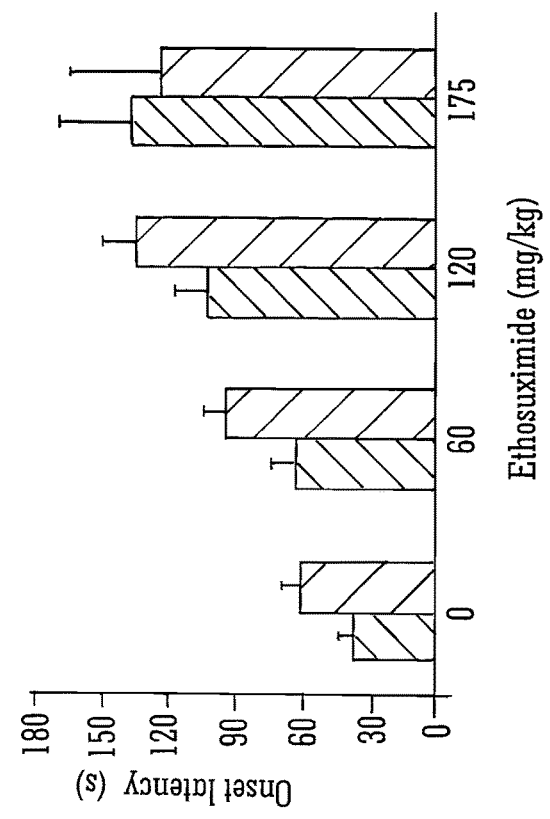
Figure 3C:
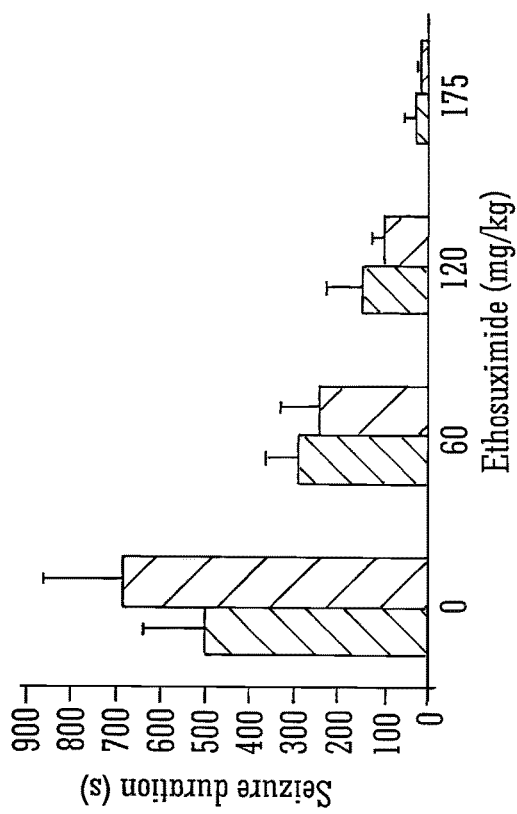

Legend to FIG. 3: A: onset latency±S.E.M. B: Severity; median values are shown in red, 25th and 75th percentiles are represented by boxes and maxima and minima in each group by error bars. C: Seizure duration±S.E.M.

Legend to FIG. 4: A: Effects of CBDV on the proportion of animals that remained seizure-free (%). B&C: Effects of CBDV on the proportion of animals that developed clonic (B) and tonic-clonic (C) seizures (%). D: Effects of CBDV on mortality (%).

Legend to FIG. 7: A: Effect of CBDV on overall seizure severity. Grey lines indicate median severity for each group, "boxes" represent 25th and 75th percentile ranges, error bars represent maxima and minima. B, C: Effect of CBDV on percentage mortality (B) and the percentage of animals that remained seizure-free (C). Seizure-free was considered to be a score of [1] or [0]. D: Onset latency (±S.E.M.) in seconds to first display of seizure severity [2] or above.

Legend to FIG. 8: A: the mean number of seizure episodes (per animal, only animals that experienced seizures were included). B: Median severity of all episodes in an experimental group, see FIG. 1 (PILO) for description of plot. C: Latency to 1st episode (±S.E.M.) in seconds. D: Mean duration of all episodes in an experimental group (±S.E.M.).

Figure 14:
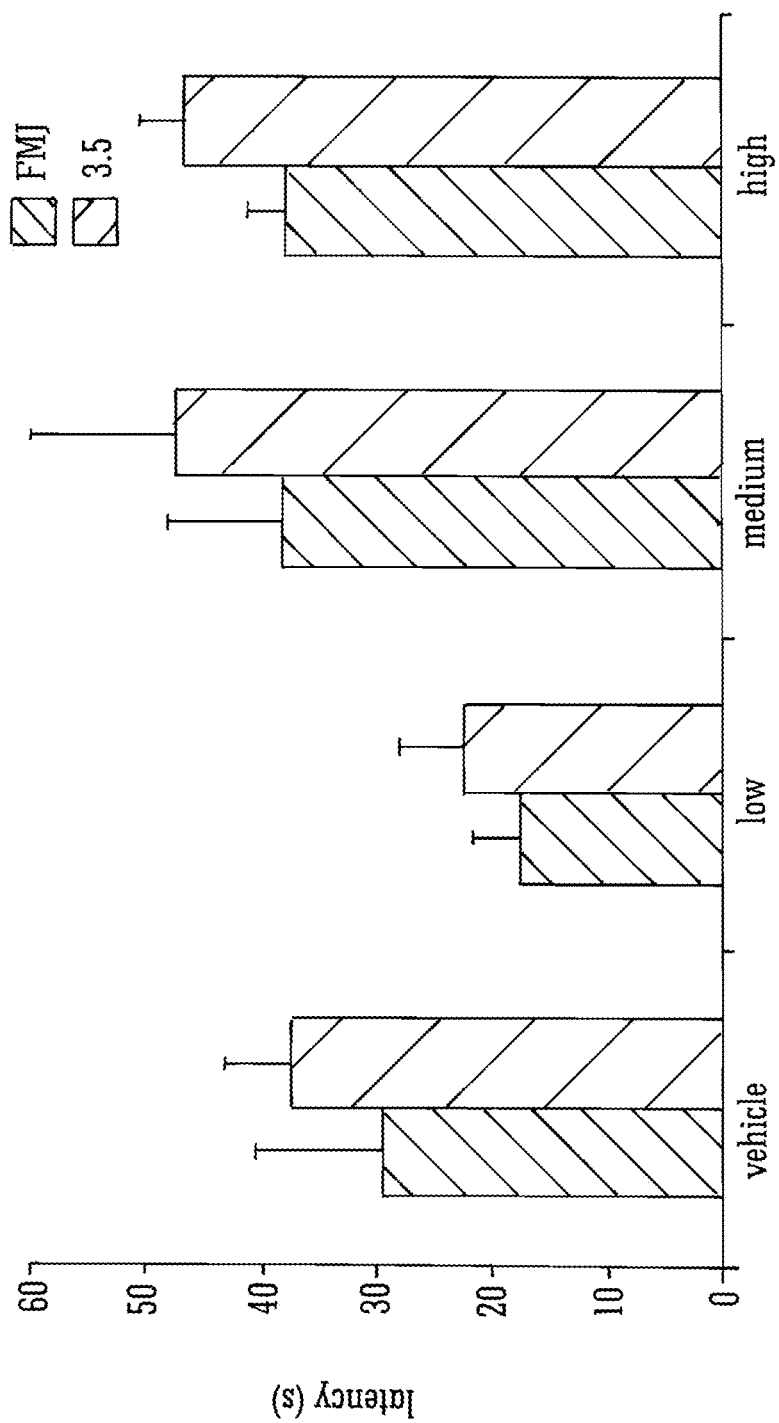
FIG. 14 shows the effects of THCV BDS and 70 mg/kg PTZ on latencies to initial and later seizure severities.

Legend to FIG. 14: The mean latencies to first myoclonic jerk (FMJ) and scores of 3.5 are shown±S.E.M. n=8-10.

Figure 15:
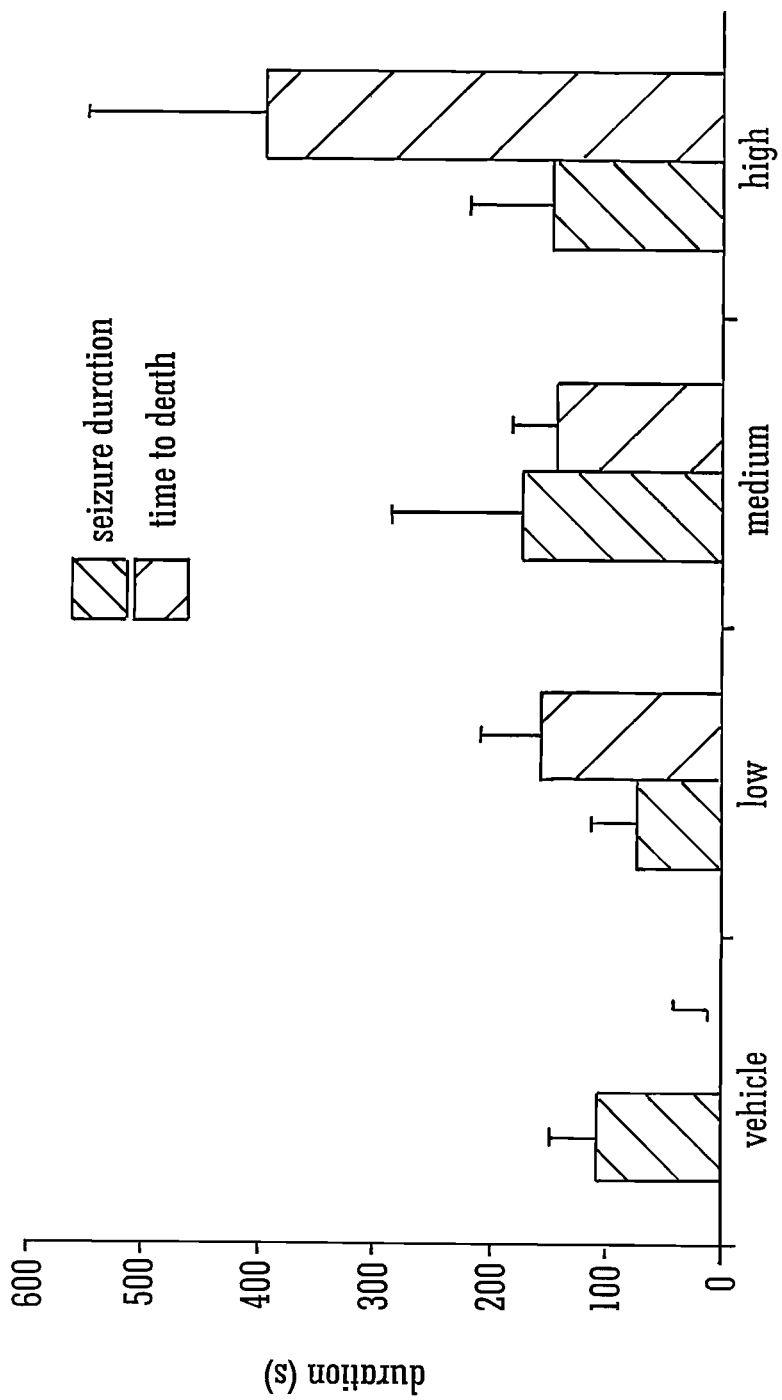
FIG. 15 shows the effects of THCV BDS and 70 mg/kg PTZ on seizure duration and time to death.

Legend to FIG. 15: The mean durations of seizures in animals that survived, and the time from first seizure sign to death in those that died, are shown±S.E.M. for vehicle or for low, medium or high doses n=3-10 dependent on proportions of animals that died within experimental groups. ∫=vehicle group had no deaths and so no value is shown here.

Figure 16:
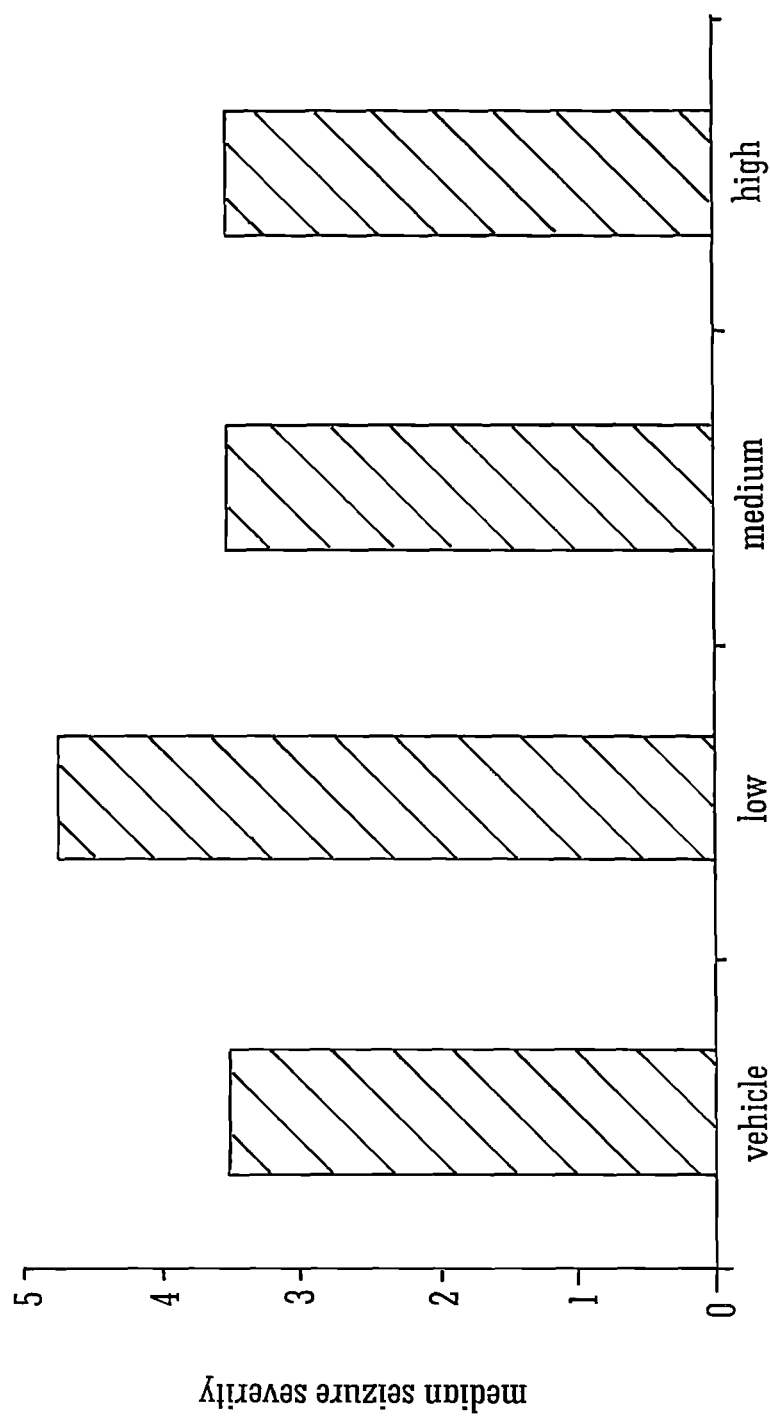
FIG. 16 shows the effects of THCV BDS and 70 mg/kg PTZ on median severity scores.

Legend to FIG. 16: Median severity scores for groups of animals treated with vehicle or with low, medium or high doses n=10 for all groups.

Figure 17:
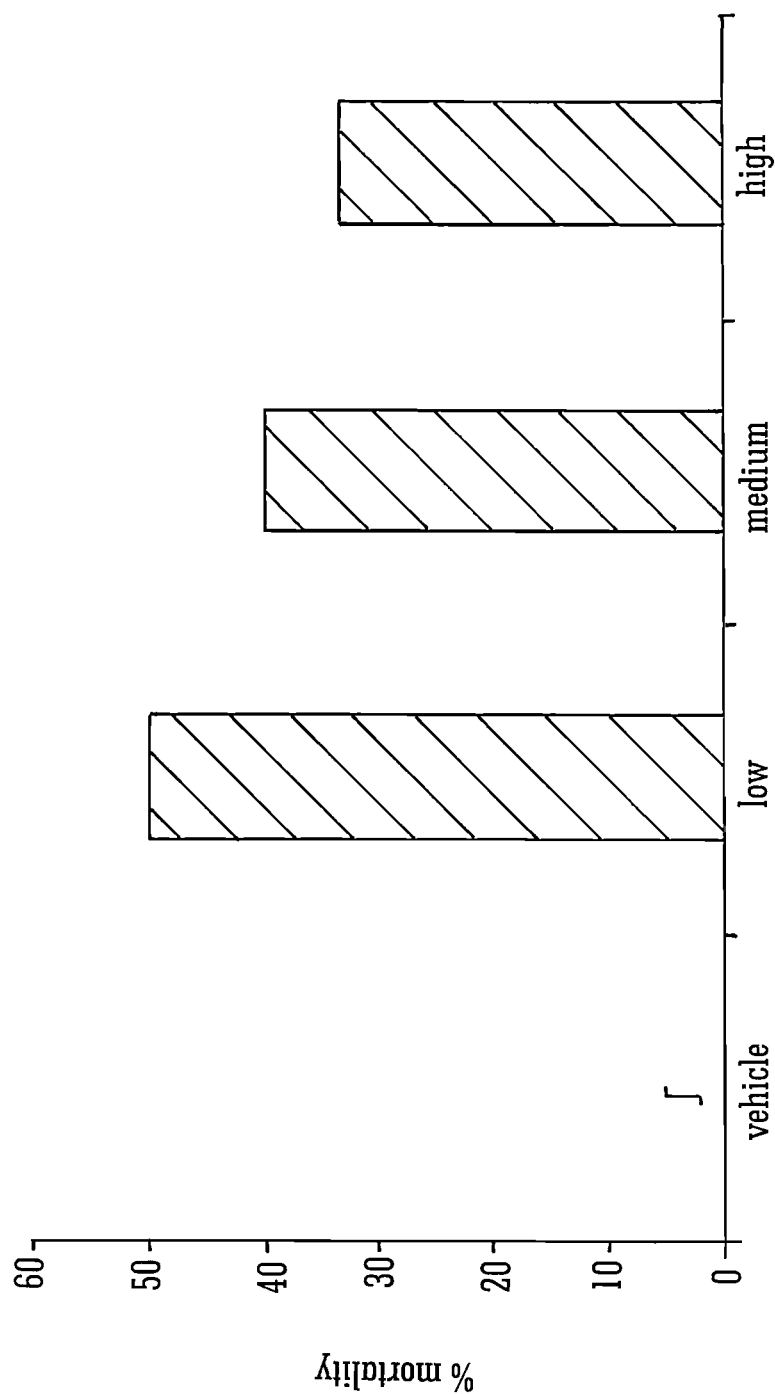
FIG. 17 shows the effects of THCV BDS and 70 mg/kg PTZ on mortality rates.

Legend FIG. 17: Mortality rates expressed as percentages for animals treated with vehicle or with low, medium or high doses. n=10 for all groups. ∫=vehicle group had no deaths, therefore no value is shown.

Figure 18:
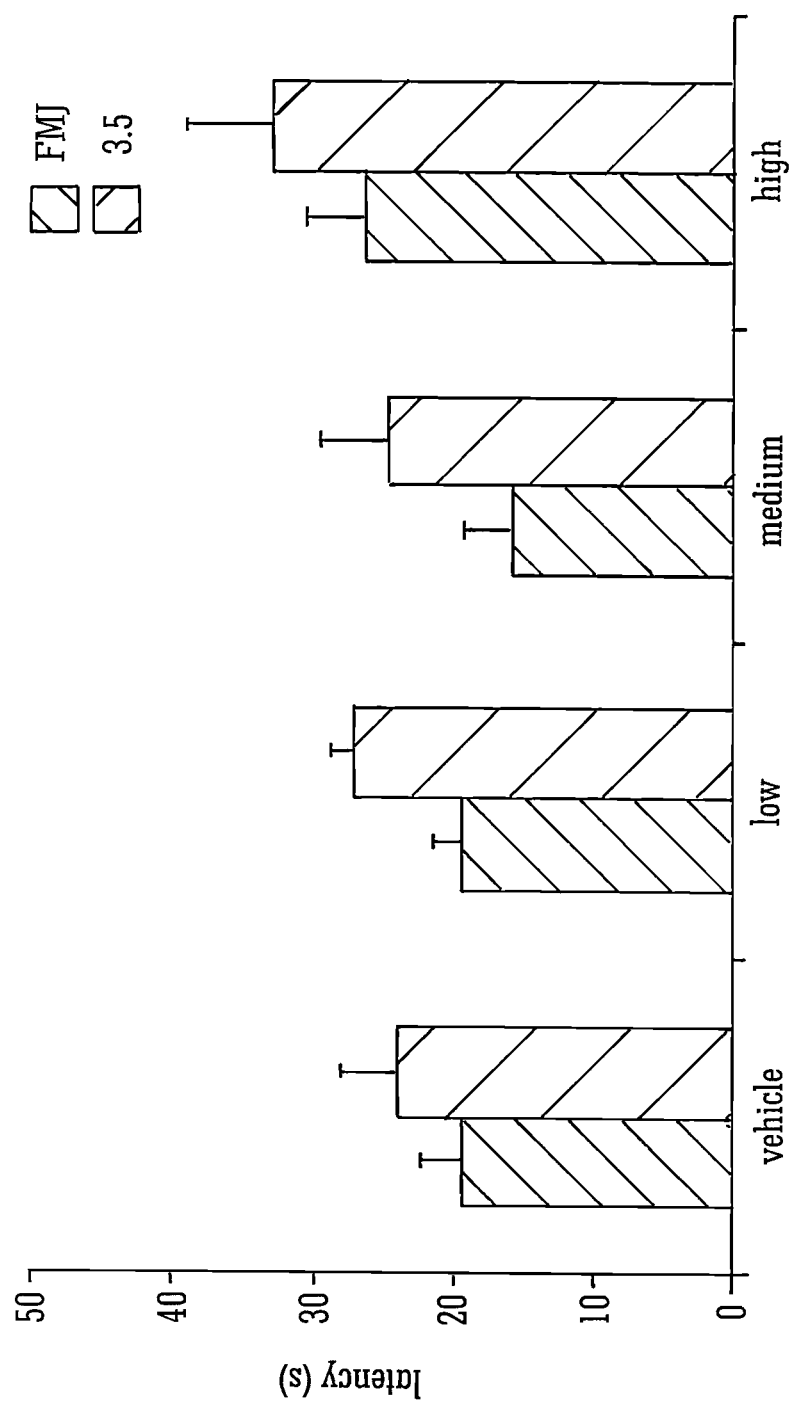
FIG. 18 shows the effects of THCV BDS and 80 mg/kg PTZ on latencies to initial and later seizure severities.

Legend to FIG. 18: The mean latencies to first myoclonic jerk (FMJ) and scores of 3.5 are shown±S.E.M. for vehicle or for low, medium or high doses. n=7-10.

Figure 19:
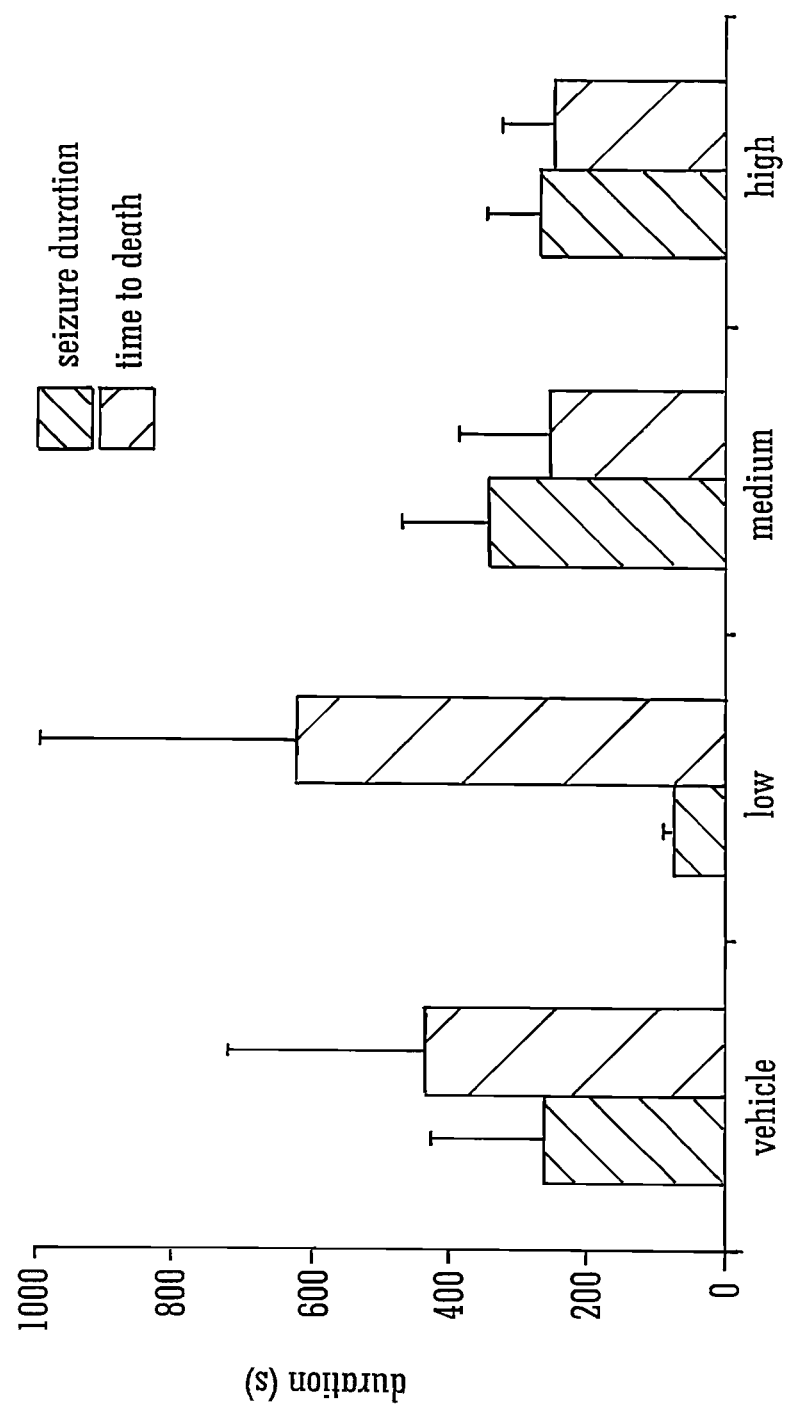
FIG. 19 shows the effects of THCV BDS and 80 mg/kg PTZ on seizure duration and time to death.

Legend to FIG. 19: The mean durations of seizures in animals that survived, and the time from first seizure sign to death in those that died, are shown±S.E.M. for vehicle or for low, medium or high doses. n=3-7 dependent on proportions of animals that died within experimental groups.

Figure 20:
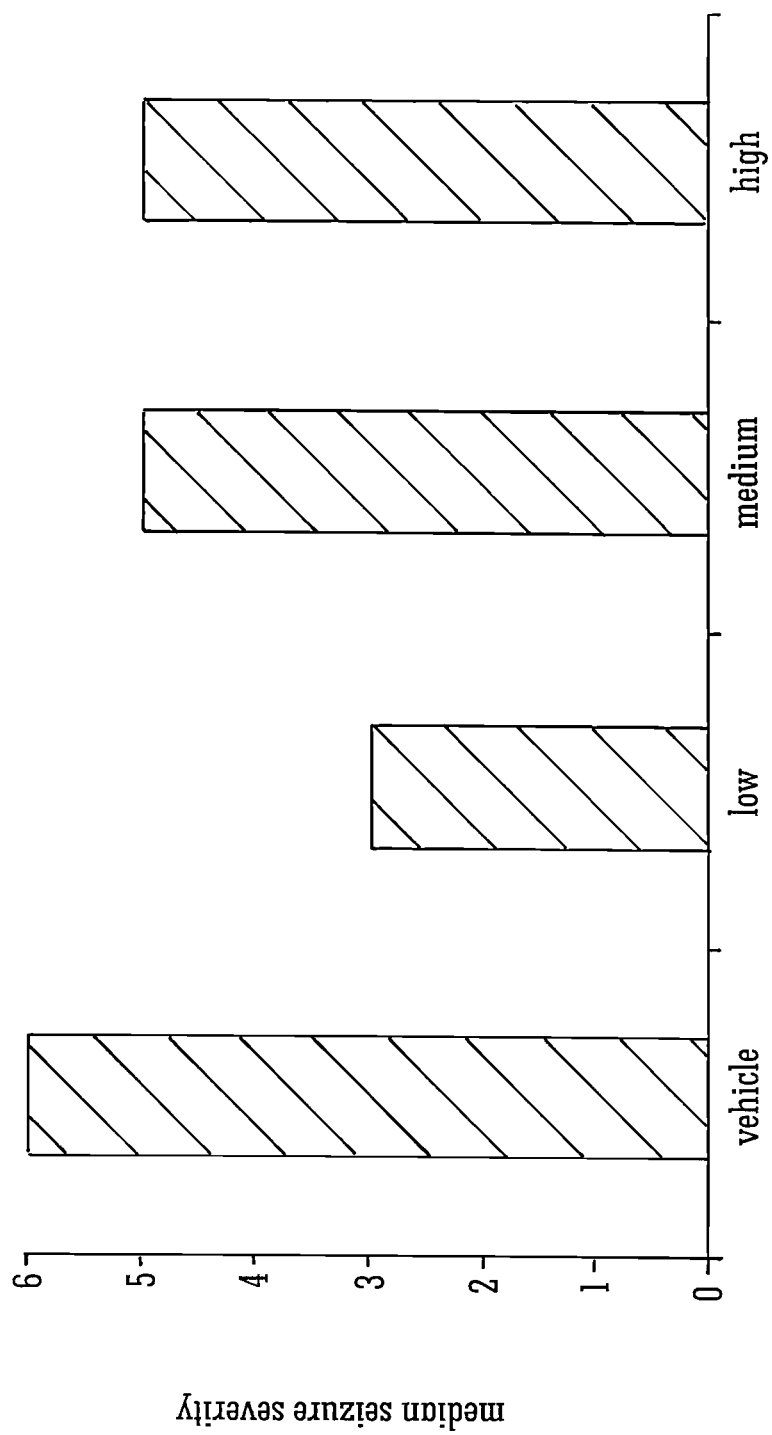
FIG. 20 shows the effects of THCV BDS and 80 mg/kg PTZ on median severity scores.

Legend to FIG. 20: Median severity scores for groups of animals treated with vehicle or with low, medium or high doses. n=10 for all groups.

Figure 21:
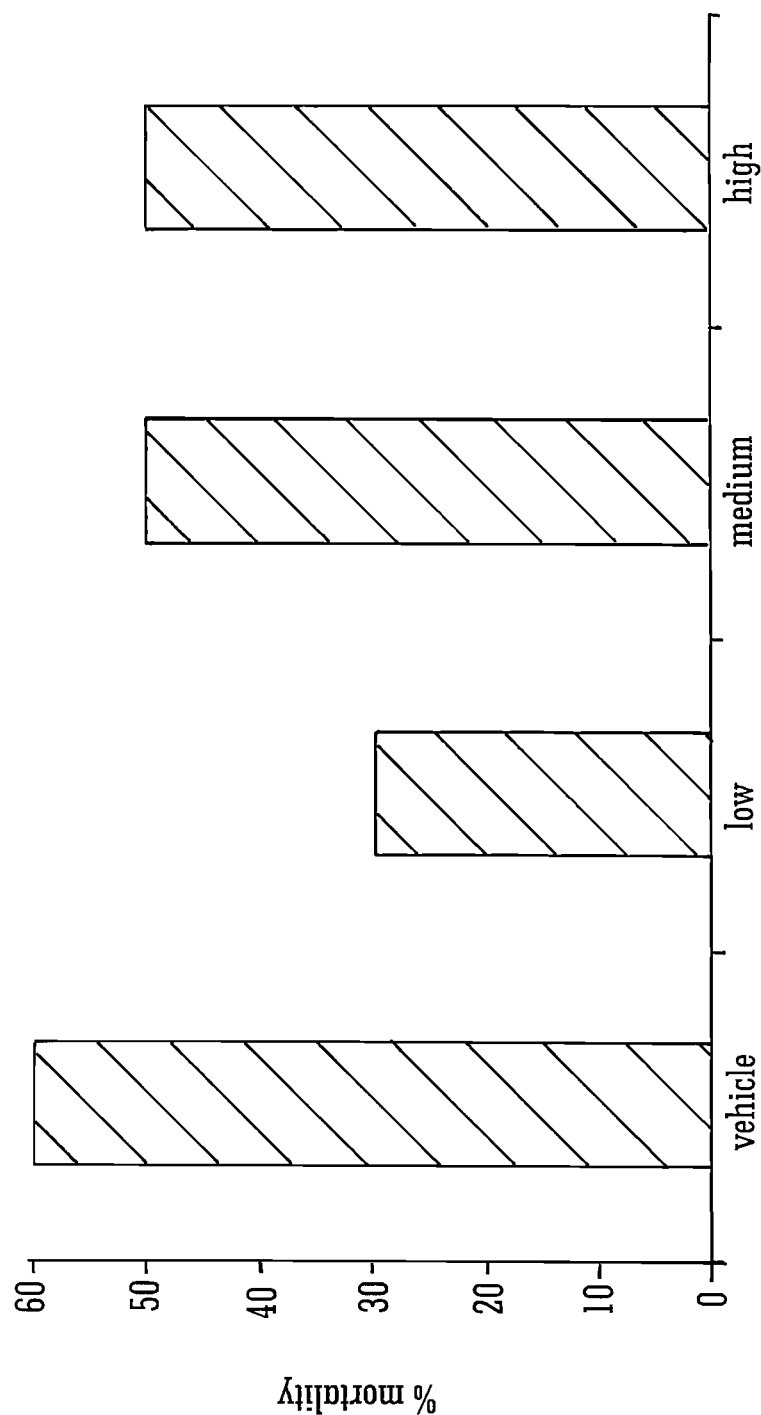
FIG. 21 shows the effects of THCV BDS and 80 mg/kg PTZ on mortality rates.

Legend to FIG. 21: Mortality rates expressed as percentages for animals treated with vehicle or with low, medium or high doses. n=10 for all groups.

Legend to FIG. 22: A, B and C show the mean latency (s) from injection of 80 mg/kg PTZ to: first sign of seizure (A); development of myoclonic seizures (B) and full tonic-clonic seizures (C) for vehicle and THCV-dosed groups. n=5-16 depending on incidence of each marker within a specific group). D shows the mean duration of seizures (s) in animals that survived post-seizure. All values±S.E.M., * indicates significant difference from vehicle group (P<0.05; Mann-Whitney U test).

Figure 23A:
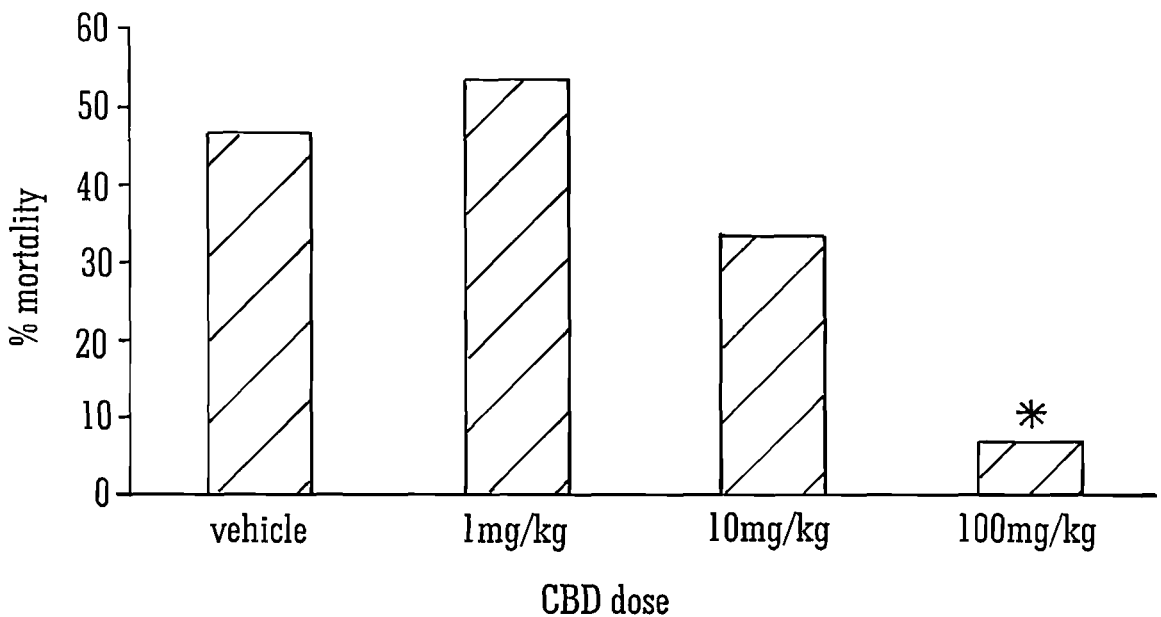
FIG. 23A-B show the effect of CBD on PTZ-induced seizures.
Figure 23B:
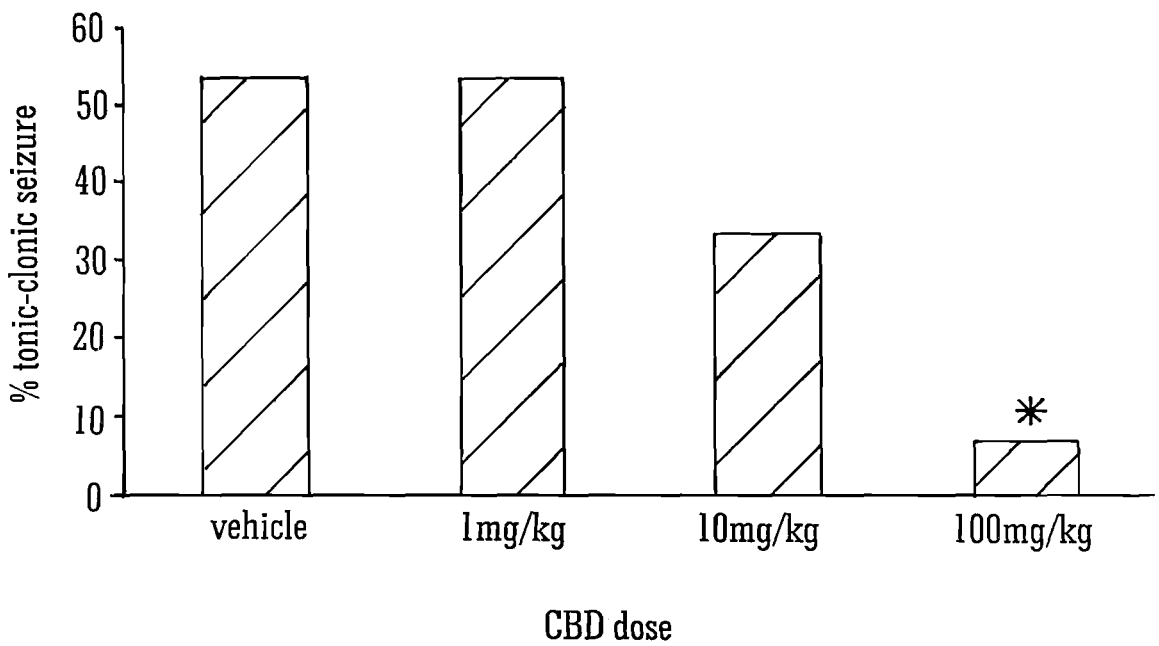

Legend to FIG. 23: A: % mortality experienced as a result of IP injection of 80 mg/kg PTZ in vehicle and CBD-dosed (1, 10, 100 mg/kg CBD) animals (n=15 for all groups). B: % of vehicle- and CBD-dosed (1, 10, 100 mg/kg CBD) animals that experienced tonic-clonic seizures as a result of IP injection of 80 mg/kg PTZ. * indicates significant result (p<0.01).

Figure 24:
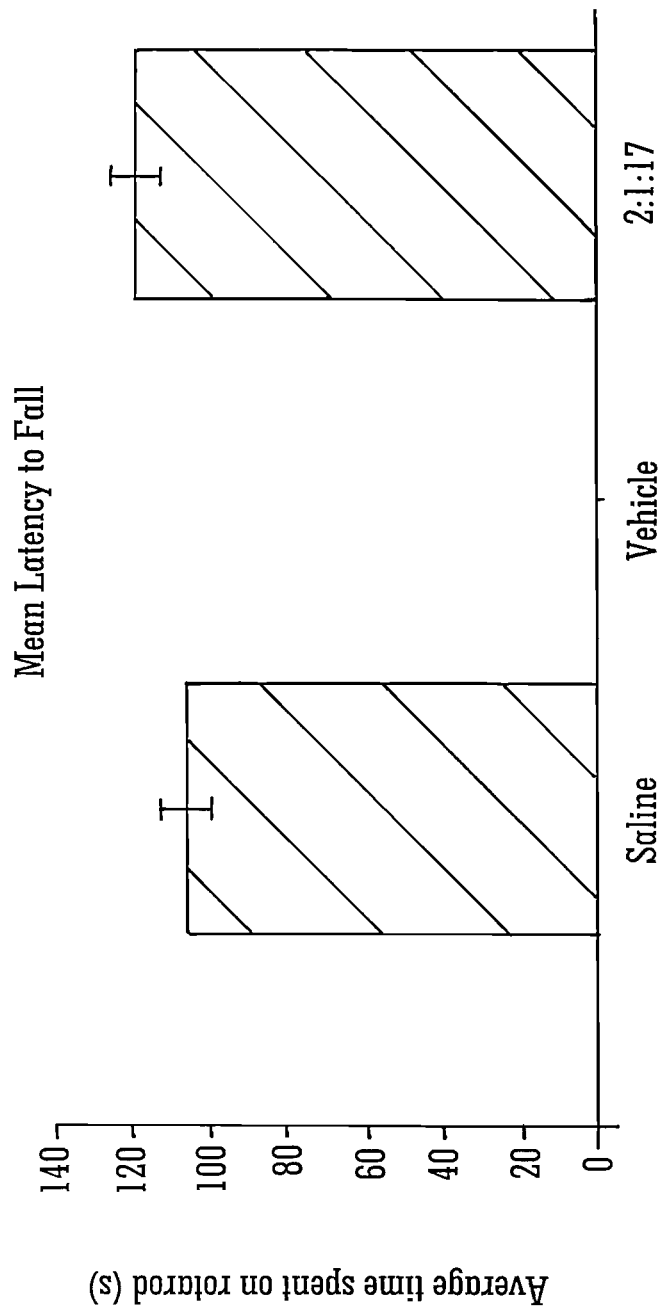
FIG. 24 shows the effect of vehicle on rotarod performance.

Legend to FIG. 24: Median latency to falling ±S.E. from the rotarod following administration of saline and 2:1:17 cremaphor:ethanol:saline.

Figure 25:
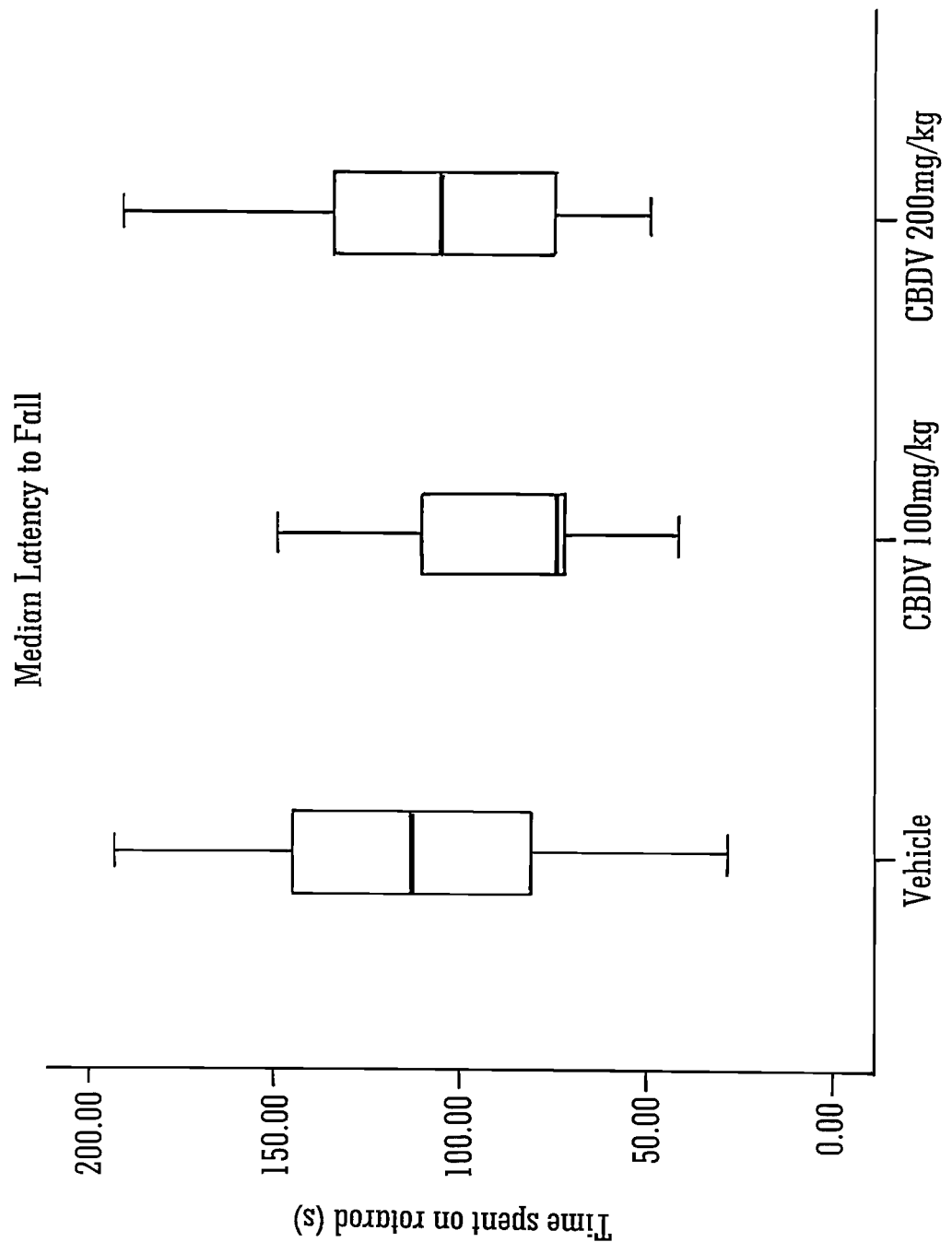
FIG. 25 shows the effect of CBDV on rotarod performance.

Legend to FIG. 25: Median latency to falling from rotarod (grey bars) with $25^{th}$ and $75^{th}$ percentiles (black boxes) and maximum and minimum values (error bars) also presented.

DETAILED DESCRIPTION

Examples 1 to 5 below describe the use of isolated CBDV in different models of epilepsy. Further examples will describe phytocannabinoid BDS which comprise along with the principal cannabinoid other secondary and minor cannabinoids along with a non-phytocannabinoid containing fraction.

EXAMPLE 1

Use of isolated CBDV in two in vitro epileptiform models in hippocampal brain slices Hippocampal slices were produced acutely from P>21 Wistar rats and activity recorded by multi-electrode arrays (MEA).

To induce epileptiform activity, either $Mg^{2+}$ was removed ($Mg^{2+}$-free model) or 100 μM 4-aminopyridine was added (4-AP model). 30 min after epileptiform burst activity was established, CBDV was added cumulatively (1, 10, 100 μM; 30 min each).

The effects of CBDV on epileptiform burst amplitude and duration were measured (Table 2.1).

Overall, CBDV at ≥10 μM or 100 μM significantly decreased burst duration and amplitude in both models with CA1 and DG regions most sensitive and CA3 least sensitive to the anti-epileptiform effects of CBDV.

TABLE 2.1

Effects of CBDV on epileptiform activity induced in the $Mg^{2+}$ free and 4-AP models

| | CBDV | Burst amplitude (% of control) | | | Burst duration (% of control) | | |
|---|---|---|---|---|---|---|---|
| | (μM) | DG | CA3 | CA1 | DG | CA3 | CA1 |
| $Mg^{2+}{}_o$- | 1 | 89.8 ± 8.6 | 112.7 ± 13.7 | 82.23 ± 10.4 | 90.6 ± 4.5 | 101.7 ± 2.3 | 99.3 ± 4.5 |
| free | 10 | 86.4 ± 3.6* | 104.8 ± 10.3 | 79.9 ± 6.9** | 92.0 ± 3.2* | 93.9 ± 4.1 | 91.2 ± 3.8* |
| model | 100 | 79.5 ± 5.6** | 102.9 ± 13.0 | 80.4 ± 8.0* | 75.6 ± 5.4** | 78.5 ± 6.6* | 74.0 ± 5.8** |
| 4-AP | 1 | 94.2 ± 3.0 | 103.0 ± 5.8 | 89.3 ± 5.6 | 95.7 ± 5.9 | 91.0 ± 6.0 | 104.3 ± 8.0 |
| model | 10 | 91.2 ± 4.9 | 121.9 ± 17.0 | 88.3 ± 5.2 | 83.8 ± 4.4** | 82.5 ± 4.8* | 85.9 ± 6.2* |
| | 100 | 95.9 ± 4.3 | 110.3 ± 7.0 | 89.5 ± 5.3* | 83.4 ± 4.1** | 79.7 ± 5.4* | 85.9 ± 5.8* |

Data is mean ± S.E.M;
*= p ≤ 0.05 and
**= p ≤ 0.01 respectively, Wilcoxon paired test.
Data from 5 rats/model, n = 9-13 electrodes.

EXAMPLE 2

Use of isolated CBDV in the PTZ model of generalised seizures

Methodology:

Animals:

Male Wistar rats (P24-29; 75-110 g) were used to assess the effects of the phytocannabinoid CBDV in the PTZ model of generalised seizures. Animals were habituated to the test environment, cages, injection protocol and handling prior to experimentation. Animals were housed in a room at 21° C. on a 12 hour light: dark cycle (lights on 0900) in 50% humidity, with free access to food and water.

The human dose equivalent (HED) can be estimated using the following formula:

$$HED = \text{Animal dose (mg/kg) multiplied by } \frac{\text{Animal } K_m}{\text{Human } K_m}$$

The $K_m$ for a rat is 6 and the $K_m$ for a human is 37.

Thus, for a human of approx 60 Kg a 200 mg/Kg dose in rat would equate to a human daily dose of about 2000 mg.

Experimental Setup:

Five 6 L Perspex tanks with lids were placed on a single bench with dividers between them. Closed-circuit television (CCTV) cameras were mounted onto the dividers to observe rat behaviour. Sony Topica CCD cameras (Bluecherry, USA) were linked via BNC cables to a low-noise PC via Brooktree digital capture cards (Bluecherry, USA). Zoneminder (http://www.zoneminder.com) software was used to monitor rats, start and end recordings and manage video files. In-house Linux scripts were used to encode video files into a suitable format for further offline analysis using The Observer (Noldus Technologies).

PTZ Model:

A range of doses of PTZ (50-100 mg/kg body weight) were used to determine the best dose for induction of seizures (see below). As a result, a dose of 80 mg/kg injected intra-peritoneally (IP; stock solution 50 mg/ml in 0.9% saline) were used to screen the CBDV.

Experimental Protocols:

On the day of testing, pure CBDV was administered via intra-peritoneal (i.p.) injection at doses of 50, 100 and 200 mg/kg alongside animals that were injected with a matched volume of the cannabinoid vehicle (2:1:17 ethanol:Cremophor: 0.9% w/v NaCl solution), which served as the negative control group. Animals were then observed for 1 hour, after which time they received an IP injection of 80 mg/kg PTZ.

Negative vehicle controls were performed in parallel with cannabinoid-dosed subjects. After receiving a dose of PTZ, animals were observed and videoed to determine the severity of seizure and latency to several seizure behaviour types (see in vivo analysis, below). Animals were filmed for half an hour after last sign of seizure, and then returned to their cage.

In Vivo Analysis:

Animals were observed during experimental procedures, but all analysis was performed offline on recorded video files using The Observer behavioural analysis software (Noldus, Netherlands). A seizure severity scoring system was used to determine the levels of seizure experienced by subjects (Pohl & Mares, 1987). All signs of seizure were detailed for all animals.

TABLE 3.1

Seizure severity scoring scale, adapted from Pohl & Mares, 1987.

| Seizure score | Behavioural expression | Righting reflex |
|---|---|---|
| 0 | No changes to behaviour | Preserved |
| 0.5 | Abnormal behaviour (sniffing, excessive washing, orientation) | Preserved |
| 1 | Isolated myoclonic jerks | Preserved |
| 2 | Atypical clonic seizure | Preserved |
| 3 | Fully developed bilateral forelimb clonus | Preserved |
| 3.5 | Forelimb clonus with tonic component and body twist | Preserved |

TABLE 3.1-continued

Seizure severity scoring scale, adapted from Pohl & Mares, 1987.

| Seizure score | Behavioural expression | Righting reflex |
|---|---|---|
| 4 | Tonic-clonic seizure with suppressed tonic phase | Lost |
| 5 | Fully developed tonic-clonic seizure | Lost |
| 6 | Death | |

Latency from Injection of PIZ to Specific Indicators of Seizure Development:

The latency (in seconds) from injection of PTZ to first myoclonic jerk (FMJ; score of 1), and to the animal attaining "forelimb clonus with tonic component and body twist" (score of 3.5) were recorded. FMJ is an indicator of the onset of seizure activity, whilst >90% of animals developed scores of 3.5, and so is a good marker of the development of more severe seizures. Data are presented as the mean±S.E.M. within an experimental group.

Maximum Seizure Severity:

This is given as the median value for each experimental group based on the scoring scale below.

% Mortality:

The percentage of animals within an experimental group that died as a result of PTZ-induced seizures. Note that the majority of animals that developed tonic-clonic seizures (scores of 4 and 5) died as a result, and that a score of 6 (death) automatically denotes that the animal also experienced tonic-clonic seizures.

Seizure Duration:

The time (in seconds) from the first sign of seizure (typically FMJ) to either the last sign of seizure or, in the case of subjects that died, the time of death—separated into animals that survived and those that did not. This is given as the mean±S.E.M. for each experimental group.

Statistics:

For measures of latency and severity, one way analysis of variance (ANOVA) was performed on the four groups together (vehicle and 50, 100 and 200 mg/kg CBDV) to detect overall effects of CBDV (p≤0.05 considered significant).

Significant ANOVA results were followed by post hoc tests to test differences between vehicle and drug groups (Tukey's test, p≤0.05 considered significant).

Results:

FIG. 1 illustrates the onset and development of seizures by showing the latency from administration of 80 mg/kg PTZ to: the onset of seizure (FIG. 1A); the development of clonic seizures (FIG. 1B) and the development of tonic-clonic seizures (FIG. 10).

A significant effect of CBDV on the latency to seizure onset was observed (p=0.041; FIG. 1A); this measure was significantly higher in animals that received 200 mg/kg CBDV than those that received vehicle alone (p=0.03).

A near-significant (p=0.055) effect of CBDV on latency to clonic seizures was observed (FIG. 1B), highlighting a significant increase in animals administered 200 mg/kg CBDV compared to vehicle-treated animals (p=0.032).

Figure 2B:
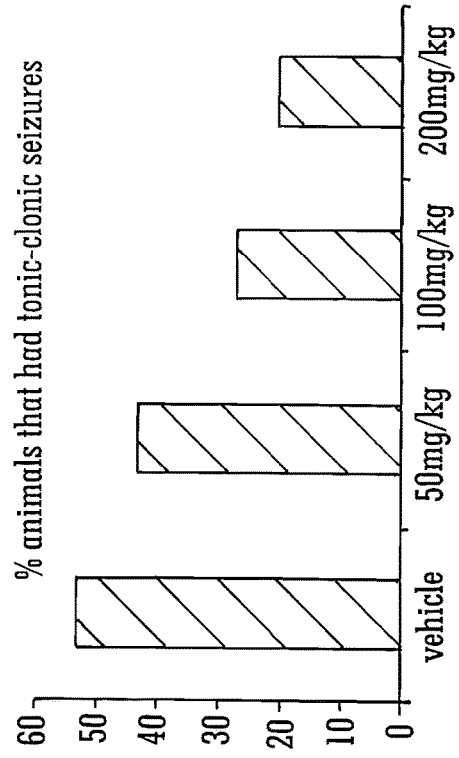
FIG. 2A-D shows the effects of CBDV on seizure severity and mortality.
Figure 2D:
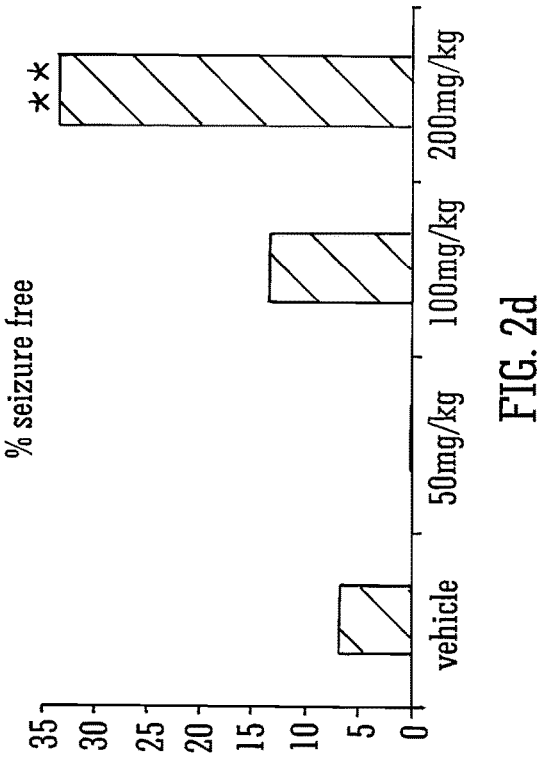

No significant effect of CBDV on latency to tonic-clonic seizures overall or at any specific dose was observed (FIG. 10) in spite of a large difference in mean value between vehicle and 200 mg/kg CBDV groups; this is likely to be due to the low number of animals treated with 200 mg/kg CBDV that developed these seizures The severity of seizures experienced by animals in the different groups was also assessed using four measures: median severity (FIG. 2A); proportion of animals that had tonic-clonic seizures (the most severe seizure type; FIG. 2B); the percentage mortality (FIG. 2C) and finally the proportion of animals that remained seizure free after PTZ administration (FIG. 2D).

Figure 2A:
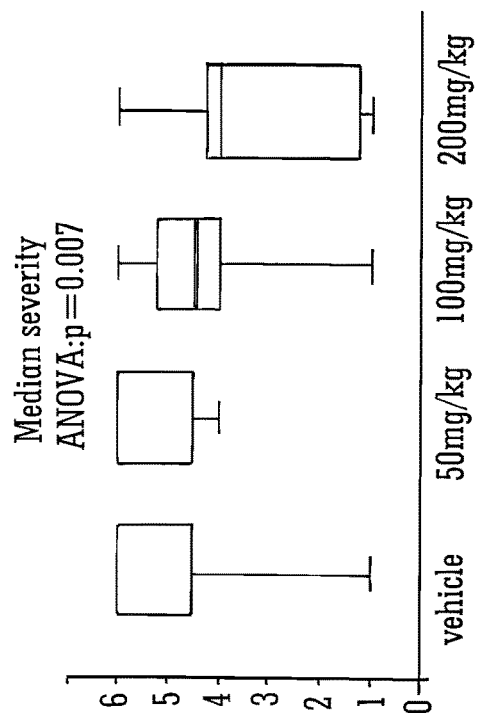

There was an overall significant effect of CBDV on seizure severity (p=0.007; FIG. 2A); animals treated with 200 mg/kg CBDV had a significantly lower median severity than those treated with vehicle alone (p=0.014).

This was reflected in a lower proportion of animals treated with 200 mg/kg CBDV reaching the most severe (tonic-clonic) seizures (3 of 15) compared to vehicle-treated animals (8 of 15; FIG. 2B; p=0.01).

This significant effect was maintained in animals treated with 100 mg/kg CBDV (4 of 15 tonic-clonic seizures; p=0.036), but not 50 mg/kg.

Figure 2C:
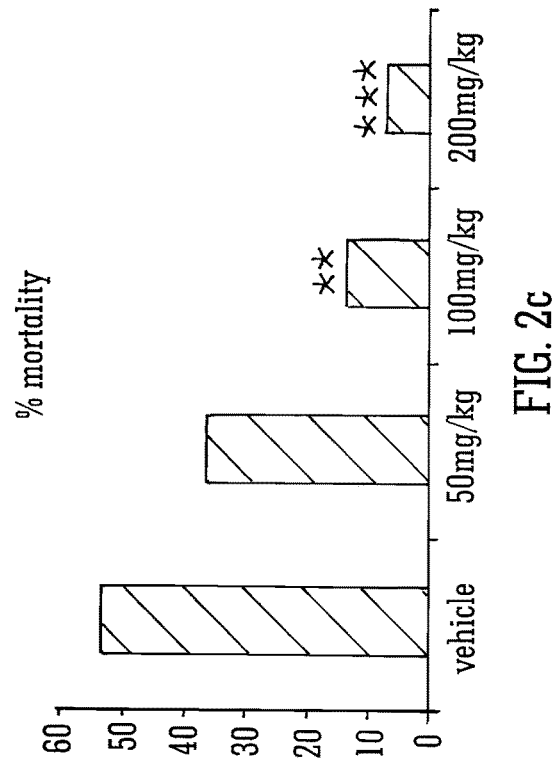

A significantly lower proportion of animals treated with 100 and 200 mg/kg CBDV (1 and 2 out of 15 respectively) died compared to the vehicle-treated group (8 of 15; p=0.002 and <0.001 respectively; FIG. 2C).

Finally, a significantly higher percentage of animals treated with 200 mg/kg CBDV experienced no seizure at all (5 of 15) compared to the vehicle group (1 of 15; p=0.003; FIG. 2D).

Conclusion:

From the above data it would appear that CBDV shows great potential as an anti-epileptic drug.

EXAMPLE 3

Use of Isolated CBDV with Standard Anti-Epileptic Drugs (SAEDs) in the PTZ Model of Generalised Seizures Methodology:

As described in Example 2 above. Varying doses of the SAED's ethosuximide and valproate were tested in combination to isolated CBDV at a dose of 200 mg/kg.

Results:

FIGS. 3 and 4 detail the use of the SAED ethosuximide (a drug operating via calcium channels) with isolated CBDV. Although the combination of the two compounds increased the onset latency, reduced seizure duration, resulted in more seizure free animals and reduced tonic/clonic seizures there was no statistically significant interaction between the two compounds. The CBDV gave similar results to valproate for mortality, however significantly CBDV was able to lessen the severity of the epilepsy to a greater degree than the existing epileptic drug valproate.

Figure 5:
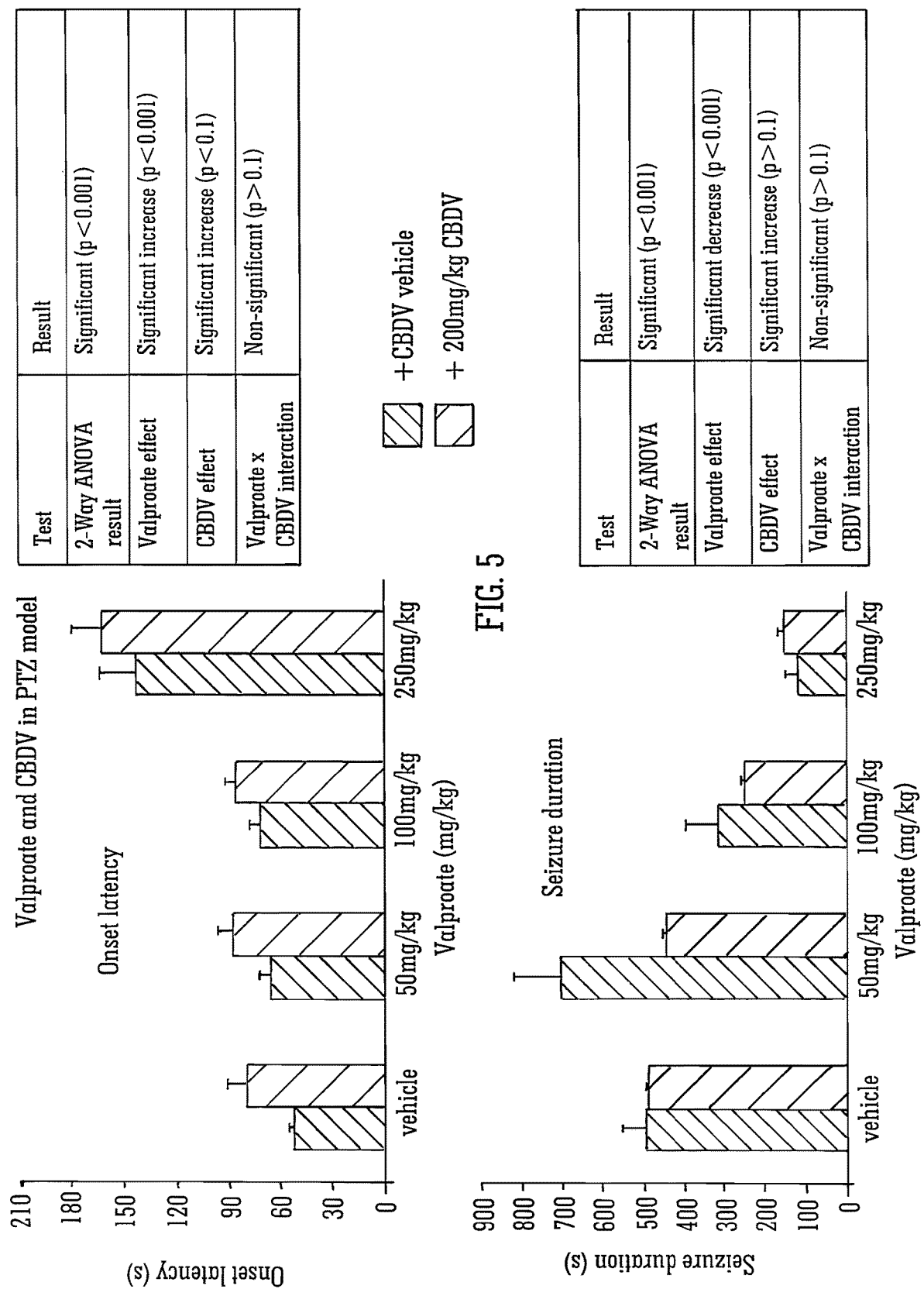
FIG. 5 shows the effect of CBDV and valproate on PTZ-induced seizures (onset latency and seizure duration)

FIGS. 5 and 6 detail the use of the SAED valproate (a drug operating via sodium channels) with isolated CBDV. When co-administered, valproate and CBDV independently induced significant decreases in onset latency, seizure severity and mortality although no synergistic effects of combinatorial administration were noted.

Both sets of results indicate benefits in their use in combination.

EXAMPLE 4

Use of Isolated CBDV in the Pilocarpine Model of Epilepsy

Methodology:

Isolated CBDV was injected intra-peritoneally (IP) in the standard vehicle (1:1:18 ethanol:Cremophor:0.9%$^w/_v$ NaCl) at doses of 50, 100 and 200 mg/kg alongside animals that received vehicle alone at a matched volume. 15 minutes later methylscopolamine (1 mg/kg; to reduce peripheral muscarinic effects of pilocarpine) was administered followed, 45 minutes later by pilocarpine (380 mg/kg, IP) administration.

Results:
FIG. 7 and 8 details the effect of CBDV on pilocarpine-induced seizures. As can be observed the lower doses of CBDV (50 and 100 mg/kg) decreased the mortality.

EXAMPLE 5

Use of Isolated CBDV with Standard Anti-Epileptic Drugs (SAEDs) in the Pilocarpine Model of Epilepsy Methodology:

As described in Example 4 above, the SAEDs valproate and phenobarbital were used at various doses along with isolated CBDV at 200 mg/kg. These two drugs are representative of two classes of anti-convulsants which have different mechanisms of action. Valproate operates via sodium channels and Phenobarbital enhances GABAergic inhibition.

Results:

FIG. 9 details the data obtained when CBDV was used in combination with the SAED valproate. Both CBDV and valproate exerted independent and positive effects upon seizure severity although only CBDV and not valproate independently caused a significant decrease in mortality. The combination of CBDV with valproate increased the seizure latency and decreased the seizure incidence. However these data were not statistically significant.

FIG. 10 details further data obtained when CBDV was used in combination with the SAED valproate. It shows that bilateral seizure incidence was significantly decreased by CBDV (particularly with the high dose Valproate (250 mg/kg).

Figure 11A:
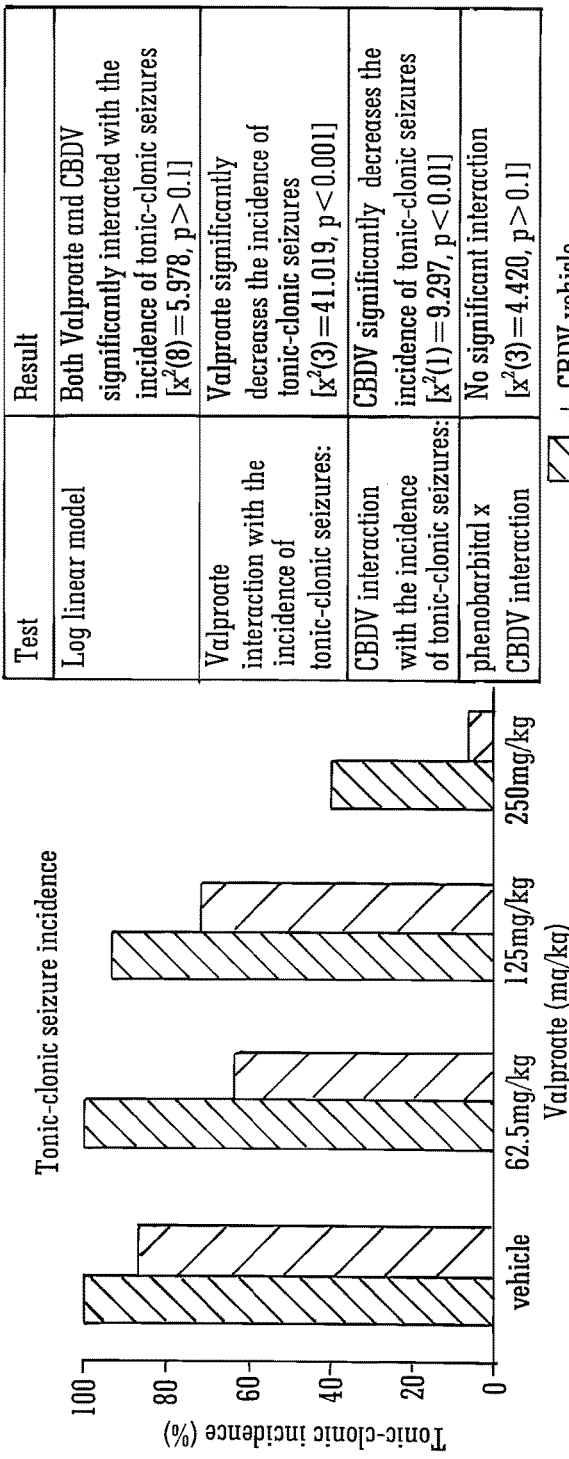
FIG. 11A-B shows the effect of high dose (200 mg/Kg) CBDV and valproate in Pilocarpine-induced seizures (tonic clonic incidence and duration)
Figure 11B:
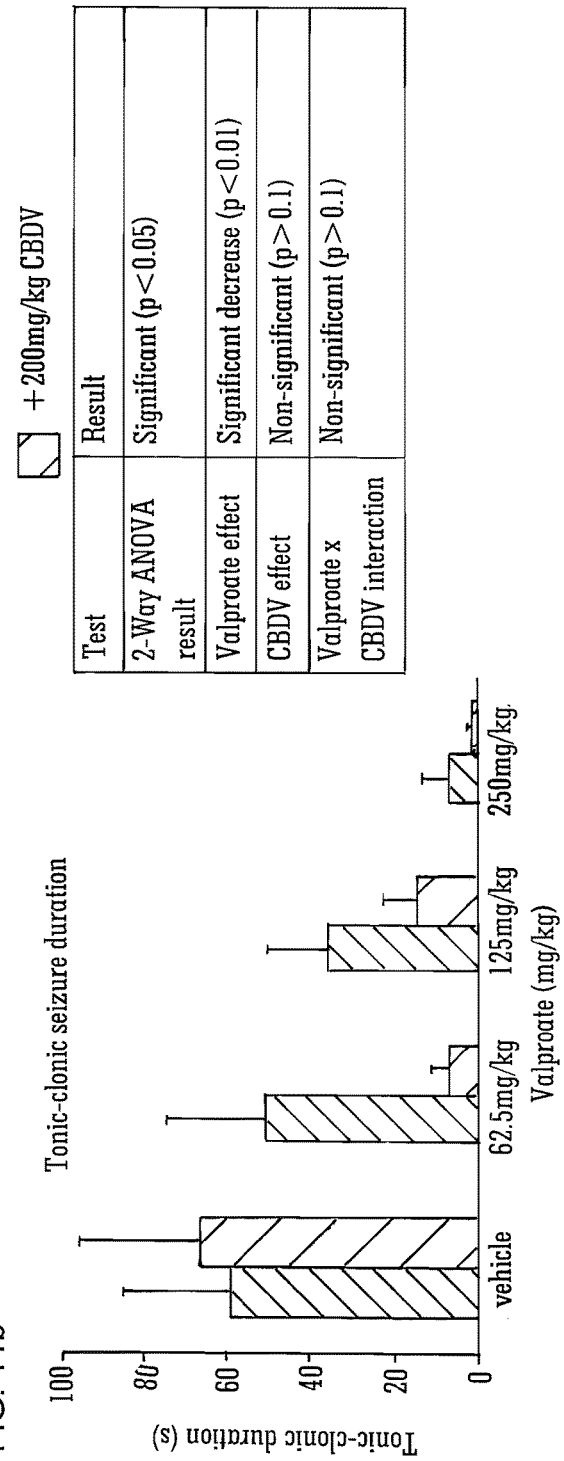

FIG. 11 details further data obtained when CBDV was used in combination with the SAED valproate. It shows that both tonic/clonic incidence and total tonic clonic duration decreased when CBDV was used in combination with all doses of Valproate and that the CBDV interaction (alone) with clonic tonic seizure was statistically significant.

Figure 12A:
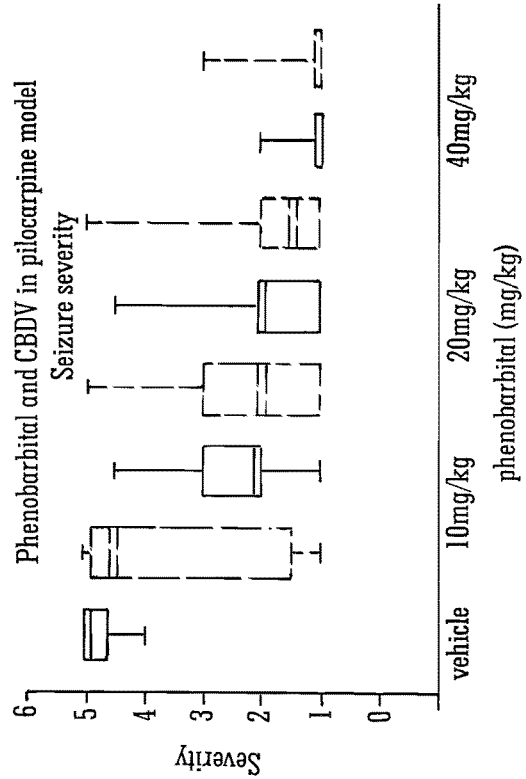
FIG. 12A-B shows the effect of CBDV and phenobarital in Pilocarpine-induced seizures (severity and mortality)
Figure 12B:
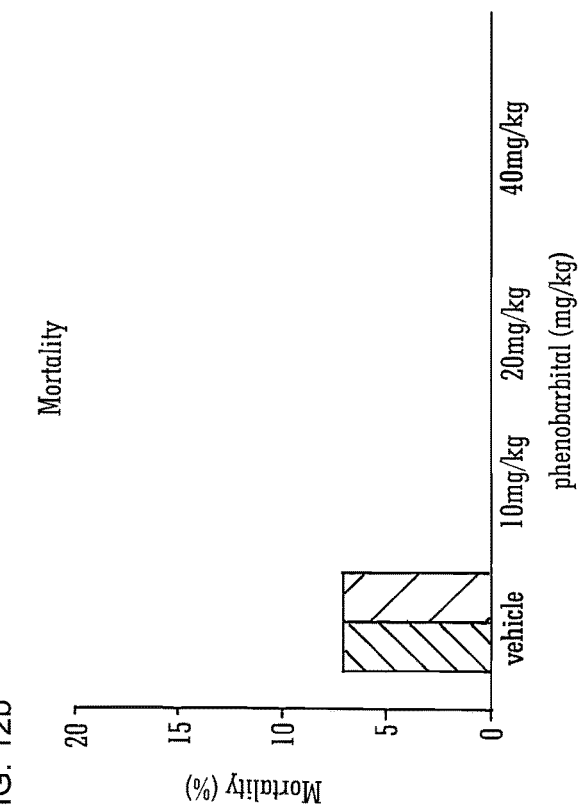

FIG. 12 details the data obtained when CBDV was used in combination with the SAED phenobarbital. As can be seen the CBDV significantly decreases severity and the combination is also significant.

Figure 13A:
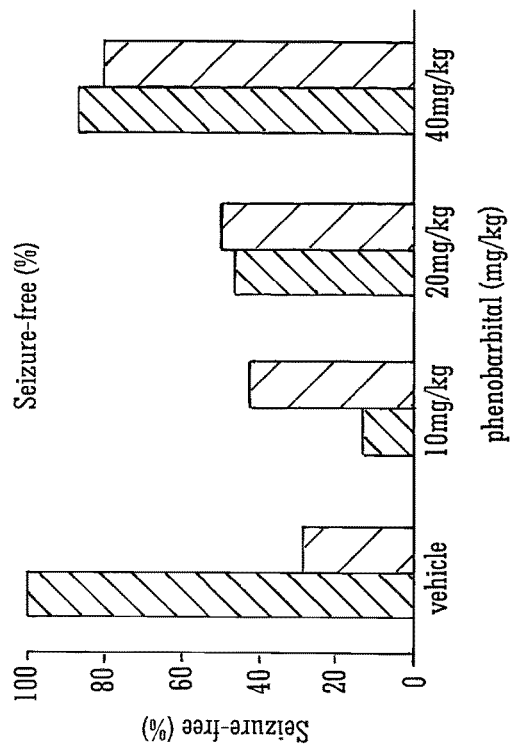
FIG. 13A-B shows the effect of CBDV and phenobarital in Pilocarpine-induced seizures (seizure free and onset latency)
Figure 13B:
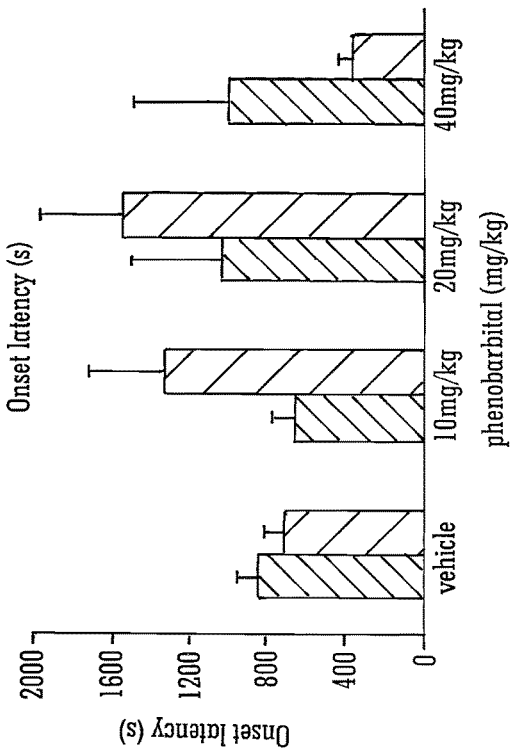

FIG. 13 details further data obtained when CBDV was used in combination with the SAED phenobarbital. Although the data did not demonstrate statistical significance there was a strong trend, particularly at the lower dose levels of Phenobarbital, towards an increase in seizure free animals and increased onset latency.

EXAMPLE 6

Analysis of Cannabinoid Botanical Edrug Substances

As described in the following example, CBDV BDS comprises, as well as CBDV, the cannabinoids CBD and THCV. Given the finding disclosed in GB0911580.9 that CBD and THCV exhibit anti-convulsant activity, a CBDV extract containing in addition to CBDV, CBD and THCV make it potentially more interesting than isolated CBDV, particularly as extracts may only possess very low amounts of THC.

Cannabidivarin (CBDV) Botanical Drug Substance Analysis

A CBDV BDS can be obtained from extraction of CBDV-rich plants. Such chemovars are bred specifically to produce a significant proportion of their cannabinoids as CBDV.

CBDV can also be prepared by adding isolated CBDV to a cannabinoid free BDS. Such a cannabinoid free BDS can be prepared from either a CBG BDS or a zero cannabinoid plant such as USO-31. Because CBG is the major cannabinoid present in CBG BDS it is possible to remove the CBG present relatively easily using standard techniques known in the art such as column chromatography. It is possible to fractionate the BDS completely so that individual compounds can be removed for purification and the remainder recombined to produce, following solvent removal, a BDS free of the selected compound(s).

The CBDV chemotype results from the breeding of plants which carry both postulated $B_D$ and $A_{PR}$ genes.

The $B_D$ gene instruct the plants to synthesize the cyclic part of the CBD molecule and the $A_{PR}$ gene instructs the plant to synthesize this molecule with a propyl side chain, as opposed to the usual pentyl chain found in CBD.

A CBDV chemovar has been bred and the BDS analysed as described in Table 4.1 below:

TABLE 4.1

Cannabidivarin BDS amount in total and range

| CBDV BDS | Amount (% w/w) | Range (±10%) | Range (±25%) | Range (±50%) |
|---|---|---|---|---|
| CBDVA | 0.14 | 0.13-0.15 | 0.11-0.18 | 0.07-0.21 |
| CBDV | 41.19 | 37.07-45.31 | 30.89-51.49 | 20.60-61.79 |
| CBDA | 0.07 | 0.06-0.08 | 0.05-0.09 | 0.04-0.11 |
| CBG | 0.59 | 0.53-0.65 | 0.44-0.74 | 0.30-0.89 |
| CBD | 17.70 | 15.93-19.47 | 13.28-22.13 | 8.85-26.55 |
| THCV | 3.06 | 2.75-6.12 | 2.30-3.83 | 1.53-4.59 |
| CBCV | 4.35 | 3.92-4.79 | 3.26-5.44 | 2.18-6.53 |
| THC | 0.88 | 0.79-0.97 | 0.66-1.10 | 0.44-1.32 |
| CBDV (related substances) | 2.20 | 1.98-2.42 | 1.65-2.75 | 1.10-3.30 |
| CBC | 0.93 | 0.84-1.02 | 0.70-1.16 | 0.47-1.40 |
| Total Cannabinoids | 71.11 | | | |
| Total Non-cannabinoids | 28.89 | | | |

The total phytocannabinoid containing fraction of CBDV BDS comprises approximately 41% of the total BDS. According to variation this fraction may vary by ±10% up to ±50%.

TABLE 4.2

Cannabidivarin BDS by percentage cannabinoid

| CBDV BDS | Amount (% of total cannabinoid) |
|---|---|
| CBDVA | 0.20 |
| CBDV | 57.92 |
| CBDA | 0.10 |
| CBG | 0.83 |
| CBD | 24.89 |
| THCV | 4.30 |
| CBCV | 6.12 |
| THC | 1.24 |
| CBDV (related substances) | 3.09 |
| CBC | 1.31 |

The amount of the principal phytocannabinoid in the CBDV BDS as a percentage of the phytocannabinoid containing fraction is approximately 58%. According to variation this fraction may vary by ±10% up to ±50%.

In this Example it is intended that references be made to the principal or secondary components independently of the 'other' cannabinoids.

The finding that the CBDV BDS comprises the known anti-epileptic phytocannabinoids CBD and THCV in relatively large amounts and relatively little THC, as compared to THCV extract below infers that the use of CBDV in the form of a BDS will be a promising new treatment for epilepsy.

Tetrahydrocannabivarin (THCV) Botanical Drug Substance Analysis

Table 4.3 below details the cannabinoid components of THCV BDS, as can be seen the secondary cannabinoid is THC and is present at a significant amount in comparison to the other cannabinoids.

TABLE 4.3

Tetrahydrocannabivarin BDS amount in total and range

| THCV BDS | Amount (% w/w) | Range (±10%) | Range (±25%) | Range (±50%) |
|---|---|---|---|---|
| CBGV | 0.15 | 0.14-0.17 | 0.11-0.19 | 0.07-0.23 |
| CBNV | 1.30 | 1.20-1.40 | 1.00-1.60 | 0.65-1.95 |
| THCV | 64.49 | 58.04-70.94 | 48.37-80.61 | 32.25-96.74 |
| CBCV | 0.65 | 0.59-0.72 | 0.49-0.81 | 0.33-0.98 |
| THC-C4 | 0.82 | 0.74-0.90 | 0.62-1.03 | 0.41-1.23 |
| CBN | 0.15 | 0.14-0.17 | 0.11-0.19 | 0.07-0.23 |
| THCVA | 0.36 | 0.32-0.40 | 0.27-0.45 | 0.18-0.54 |
| THC | 13.43 | 12.09-14.77 | 10.07-16.79 | 7.72-20.15 |
| Unknowns | 0.58 | 0.52-0.64 | 0.44-0.73 | 0.29-0.87 |
| Total Cannabinoids | 81.93 | | | |
| Total Non-cannabinoids | 18.07 | | | |

The total phytocannabinoid containing fraction of THCV BDS comprises approximately 74-90% (w/w) of the total BDS.

TABLE 4.4

Tetrahydrocannabivarin BDS by percentage cannabinoid

| THCV BDS | Amount (% of total cannabinoid) |
|---|---|
| CBGV | 0.18 |
| CBNV | 1.59 |
| THCV | 78.71 |
| CBCV | 0.79 |
| THC-C4 | 1.00 |
| CBN | 0.18 |
| THCVA | 0.44 |
| THC | 16.39 |
| Unknowns | 0.71 |

The amount of the principal phytocannabinoid in the THCV BDS as a percentage of the phytocannabinoid containing fraction is approximately 71-87% (w/w). The THCV BDS also has a secondary cannabinoid THC which is present at approximately 14.8-18% (w/w) of the phytocannabinoid containing fraction.

Non-Cannabinoid Containing Components

The non-cannabinoid components of a phytocannabinoid BDS may play an important role in the BDS's pharmacology. As such the terpene profile is classified below. The following tables illustrate the terpene profile of a CBD chemovar which is representative of a high phytocannabinoid containing plant. Five plants were freshly harvested and extracted using steam distillation. The principal monoterpene and sesquiterpene are highlighted in bold.

TABLE 4.5

Monoterpene amount by percentage of total terpene fraction and ranges

| Monoterpenes | Amount (% of terpene fraction) | Range (±10%) | Range (±25%) | Range (±50%) |
|---|---|---|---|---|
| Pinene (alpha & beta) | 10.56 | 9.50-11.62 | 7.92-13.20 | 5.28-15.84 |
| Myrcene | 39.46 | 35.51-43.41 | 29.60-49.33 | 19.73-59.19 |
| Limonene | 4.14 | 3.73-4.55 | 3.11-5.18 | 2.07-6.21 |
| Beta-ocimene | 4.04 | 3.64-4.44 | 3.03-5.05 | 2.02-6.06 |
| Total | 58.20 | | | |

The monoterpene containing fraction comprises approximately 52-64% (w/w) of the total terpene fraction.

TABLE 4.6

Monoterpene amount by percentage of monoterpenes

| Monoterpenes | Amount (% of monoterpene fraction) |
|---|---|
| Pinene (alpha & beta) | 18.14 |
| Myrcene | 67.80 |
| Limonene | 7.12 |
| Beta-ocimene | 6.94 |

The amount of the principal monoterpene myrcene in the monoterpene fraction as a percentage of the monoterpene fraction is approximately 61-75% (w/w). The monoterpene fraction also has a secondary monoterpene pinene which is present at approximately 16.3-20% (w/w) of the monoterpene fraction.

TABLE 4.7

Sesquiterpene amount by percentage of total terpene fraction and ranges

| Sesquiterpenes | Amount (% of terpene fraction) | Range (±10%) | Range (±25%) | Range (±50%) |
|---|---|---|---|---|
| Caryophyllenes (t & oxide) | 29.27 | 26.34-32.20 | 21.95-36.59 | 14.64-43.91 |
| Bergotamene | 0.18 | 0.16-0.20 | 0.14-0.23 | 0.09-0.27 |
| Humulene | 7.97 | 7.17-8.77 | 5.98-9.96 | 3.99-11.96 |
| Aromadendrene | 0.33 | 0.30-0.36 | 0.25-0.41 | 0.17-0.50 |
| Selinene | 0.59 | 0.53-0.65 | 0.44-0.74 | 0.30-0.89 |
| Anon | 0.44 | 0.40-0.48 | 0.33-0.55 | 0.22-0.66 |
| Farnesene (Z, E & alpha) | 1.55 | 1.40-1.71 | 1.16-1.94 | 0.78-2.33 |
| alpha Gurjunene | 0.12 | 0.11-0.13 | 0.09-0.15 | 0.06-0.18 |
| Bisabolene | 0.39 | 0.35-0.43 | 0.29-0.49 | 0.20-0.59 |
| Nerolidol | 0.43 | 0.39-0.47 | 0.32-0.54 | 0.22-0.65 |
| Diepicedrene-1-oxide | 0.38 | 0.34-0.42 | 0.29-0.48 | 0.19-0.57 |
| Alpha-Bisabolol | 0.16 | 0.14-0.18 | 0.12-0.20 | 0.08-0.24 |
| Total | 41.80 | | | |

The sesquiterpene containing fraction comprises approximately 27-32% (w/w) of the total terpene fraction.

TABLE 4.8

Sesquiterpene amount by percentage of sesquiterpenes

| Sesquiterpenes | Amount (% of sesquiterpene fraction) |
|---|---|
| Caryophyllenes (t & oxide) | 70.02 |
| Bergotamene | 0.43 |
| Humulene | 19.07 |
| Aromadendrene | 0.79 |
| Selinene | 1.41 |
| Anon | 1.05 |
| Farnesene (Z, E & alpha) | 3.71 |
| alpha Gurjunene | 0.29 |
| Bisabolene | 0.93 |
| Nerolidol | 1.03 |
| Diepicedrene-1-oxide | 0.91 |
| Alpha-Bisabolol | 0.38 |

Patent application number PCT/GB2008/001837 describes the production of a 'zero cannabinoid' plant. These plants were produced by selective breeding to produce a *Cannabis sativa* L plant that contained a generally qualitatively similar terpene profile as a *Cannabis sativa* L plant that produced cannabinoids yet it was devoid of any cannabinoids. These plants can be used to produce cannabinoid-free plant extracts which are useful control plants in experiments and clinical trials. A breakdown of the terpene profile produced in the plants can be found in the table below. The primary monoterpenes and sesquiterpene are highlighted in bold.

TABLE 4.9

Monoterpene amount by percentage of total terpene fraction and ranges

| Monoterpenes | Amount (% of terpene fraction) | Range (±10%) | Range (±25%) | Range (±50%) |
|---|---|---|---|---|
| Pinene (alpha & beta) | 29.34 | 26.41-32.27 | 22.01-36.68 | 14.67-44.01 |
| Myrcene | 29.26 | 26.33-32.19 | 21.95-36.58 | 14.63-43.89 |
| Limonene | 5.32 | 4.79-5.85 | 3.99-6.65 | 2.66-7.98 |
| Linalol | 4.50 | 4.05-4.95 | 3.38-5.63 | 2.25-6.75 |
| Verbenol (cis & trans) | 3.45 | 3.11-3.80 | 2.59-4.31 | 1.73-5.18 |
| Total | 71.87 | | | |

The monoterpene containing fraction comprises approximately 65-79% (w/w) of the total terpene fraction.

TABLE 4.10

Monoterpene amount by percentage of monoterpenes

| Monoterpenes | Amount (% of monoterpene fraction) |
|---|---|
| Pinene (alpha & beta) | 40.82 |
| Myrcene | 40.71 |
| Limonene | 7.41 |
| Linalol | 6.26 |

The zero cannabinoid plant was found to comprise two principal monoterpenes; pinene and myrcene. The amount of the principal monoterpene myrcene in the monoterpene fraction as a percentage of the monoterpene fraction is approximately 37-45% (w/w). The amount of the principal monoterpene pinene in the monoterpene fraction as a percentage of the monoterpene fraction is approximately 37-45% (w/w).

EXAMPLE 7

Use of CBDV (BDS) in the PTZ Model of Generalised Seizures

Methodology as described in Example 2.

CBDV BDS was administered at four doses that yielded a dose of CBDV of 50 and 100 mg/kg. Table 7.1 below details the data obtained.

TABLE 7.1

| CBDV (mg/kg) | Mortality (%) |
|---|---|
| 0 | 26.3 |
| 50 | 16.7 |
| 100 | 0 |

As can be seen the CBDV BDS exhibited a trend to decrease seizure-related mortality.

In contrast to the SAEDs, in all of the experiments using both isolated CBDV and CBDV BDS, animals did not exhibit any notable side effects. This makes this novel anti-convulsant an attractive compound for use either alone or in combination in the treatment of epilepsy.

EXAMPLE 8

Use of THCV (BDS), Isolated THCV and Isolated CBD in Models of Epilepsy

The data demonstrating the activity of THCV BDS and isolated THCV and CBD are given below in support of the likely benefit of a CBDV extract containing CBD and THCV as well as a non-cannabinoid fraction.

General methodology is as described in Example 2.

Results:

The THCV BDS comprised a whole extract of a chemovar in which THCV was the predominant cannabinoid. (i.e. it was the major cannabinoid present in the extract, 80% by weight of the total cannabinoid content). THC was the second most prevalent cannabinoid, and was present in significant amounts. (i.e. it comprised greater than 10% by weight of the total cannabinoid content, being present at about 16%), and there were a number of minor cannabinoids identified, each comprising less than 2% by weight of the total cannabinoid content as measured by HPLC analysis. The ratio of THCV to THC in this extract is about 5:1.

In fact the THCV content was 67.5% by weight of the extract and the THC content was 13.6% by weight of the extract, with the other identified cannabinoids in total comprising about 3% by weight of the extract, the remaining 16% comprising non-cannabinoids.

PTZ Pilot Study

Seizures induced by a range of PTZ concentrations (50-100 mg/kg; the range present in the literature) in rats were investigated to determine an optimal dose prior to the investigation of the cannabinoid effect. PTZ doses of:

50 mg/kg and 60 mg/kg induced very little seizure-like activity (n=4);

70 mg/kg typically induced clonic seizures (score of 3.5; 8 of 13 subjects);

80 mg/kg regularly induced tonic-clonic seizures (scores of 4 and 5; 6 of 10 subjects).

Additionally, it was found that repeated dosing with PTZ resulted in increased sensitivity over time; therefore no experiments were performed on animals that had already received a dose of PTZ.

The effect of THCV BDS on PTZ-induced seizures was first assessed against a PTZ dose of 70 mg/kg. As described below, this yielded a vehicle control group that did not typically experience severe seizure scores. Therefore THCV BDS was also screened against an 80 mg/kg dose of PTZ. It was felt that the increased seizure severity experienced by vehicle control animals exposed to 80 mg/kg PTZ was a more appropriate test of potential anti-convulsant activity.

Effect of THCV BDS on Moderately Severe (70 mg/kg) PTZ-Induced Seizures

Three doses of THCV BDS were assessed against a concentration of PTZ known to induce moderate seizures in rats (70 mg/kg; see pilot, above). The low, medium and high doses of THCV BDS used were 0.37, 3.70 and 37.04 mg/kg, and yielded actual THCV doses of 0.25, 2.5 and 25 mg/kg respectively. These doses were matched by THCV content to those being used for screening pure THCV against PTZ-induced seizures.

THCV BDS did not have any significant effects on latency to first myoclonic jerk or on latency to attaining a severity score of 3.5 on the seizure severity scale (FIG. 14). It should be noted that although values for both these variables were higher for animals treated with medium and high dose THCV BDS compared to control, this failed to reach significance ($P>0.05$). Similarly, no significant impact on duration of seizure was seen (FIG. 15).

The effects of THCV BDS on seizure severity (FIG. 16) and mortality (FIG. 17) in animals that received doses of 70 mg/kg PTZ did not conform to a simple pattern. No animal injected with vehicle-alone exceeded the median severity score of 3.5 for that group, and no animals died (n=10).

In contrast, 70 mg/kg PTZ induced severe tonic-clonic seizures and death in 50% of animals injected with a low dose of THCV BDS, demonstrating a median severity score of 4.75. This increase in severity was not significant. However, animals injected with medium and high doses of THCV BDS exhibited a lower median severity score and lower mortality rates than those exposed to low doses (FIGS. 16 & 17). Medium and high dose mortality rates were higher than that of the vehicle group, but not significantly so ($P>0.05$; FIG. 17). However, median severity scores were the same between medium & high doses (FIG. 16). This pattern of results suggested that a further set of experiments, in which THCV BDS was screened against a dose of PTZ which would induce severe seizures in control (vehicle-treated) animals, was required.

Effect of THCV BDS on Severe (80 mg/kg) PTZ-Induced Seizures

The effects of the same three doses of THCV BDS on seizures induced by 80 mg/kg PTZ were assessed. It is worth noting that 80 mg/kg induced significantly more severe seizures than 70 mg/kg in vehicle control groups ($P=0.009$), with median seizure severity scores of 6 and 3.5 respectively. THCV BDS did not have a significant effect on latencies to FMJ or a severity score of 3.5 (FIG. 18). Similarly, no effect was observed on seizure durations (FIG. 19).

Low dose THCV BDS decreased both seizure severity (FIG. 20) and mortality (FIG. 21) in animals that received doses of 80 mg/kg PTZ. Animals that received low THCV BDS had a lower median severity score (3.5 compared to 6) than vehicle controls. However, this difference was not significant ($P>0.5$). The low THCV BDS dose group also had a mortality rate half that of the vehicle control group (30% vs 60%).

Groups treated with medium and high doses of THCV BDS had a lower seizure severity score of 4.75 ($P>0.5$ vs control), and a lower mortality rate of 50%, compared to 6 and 60% respectively.

In Vivo Summary and Conclusion

Screening of THCV BDS in the PTZ model did not appear to have any significant anti- or pro-convulsant effects on either moderate or severe PTZ-induced seizures. However, a trend towards lower severity and mortality was seen in animals that received a low dose of THCV BDS prior to induction of severe (80 mg/kg PTZ) seizures, compared to vehicle controls.

It is possible that this effect is masked at higher doses of THCV BDS by higher levels of other cannabinoid constituents (such as THC) present in the non-THCV content of the THCV BDS. Higher doses of THCV BDS will contain increasing doses of non-THCV content, such as THC, which may oppose any potential positive effects of THCV.

Isolated THCV:

Effect of Isolated THCV Against PTZ-Induced Seizures

Low (0.025 mg/kg), medium (0.25 mg/kg) and high (2.5 mg/kg) doses of pure THCV were assessed for their effects on PTZ-induced seizures. It is worth noting at this point, for comparisons to THCV BDS, that differing doses of pure THCV were used compared to THCV BDS. See Table 8.1 below.

TABLE 8.1

Comparison of THCV BDS and pure THCV doses used in PTZ model

| Test CB | "low" dose (mg/kg) | "medium" dose (mg/kg) | "high" dose (mg/kg) |
|---|---|---|---|
| THCV BDS | 0.25 | 2.5 | 25 |
| Pure THCV | 0.025 | 0.25 | 2.5 |

Values given are for effective THCV content of doses (therefore actual doses of THCV BDS are approx 1.5 times larger).

80 mg/kg PTZ successfully induced seizures of varying severities in animals from all 4 experimental groups (n=16 per group). PTZ-induced seizures led to the death of 44% of animals that received vehicle alone. Groups that received low, medium and high THCV all exhibited lower mortality rates of 41%, 33% and 38% respectively; however these values were not significantly different from that of the vehicle group ($p>0.05$, binomial test).

The mean values for latency to first seizure sign, and to scores of [3] and [5] on the seizure scoring scale used, as well as the duration of seizure for surviving animals, are described in FIGS. 22A-D.

It can be seen that seizures started later, as shown by increased latency to first manifestation of seizure-like behaviour (FIG. 22A) in animals that received THCV compared to vehicle controls.

The delay of onset was significant at the highest dose of THCV ($p=0.02$). A similar pattern was seen for latencies to scores of [3] and [5] (FIGS. 22B and 22C) with all THCV doses exhibiting increased latencies, reaching a significant level at the highest dose of THCV ($p=0.017$ and 0.013 for [3] and [5] respectively).

Figure 22A:
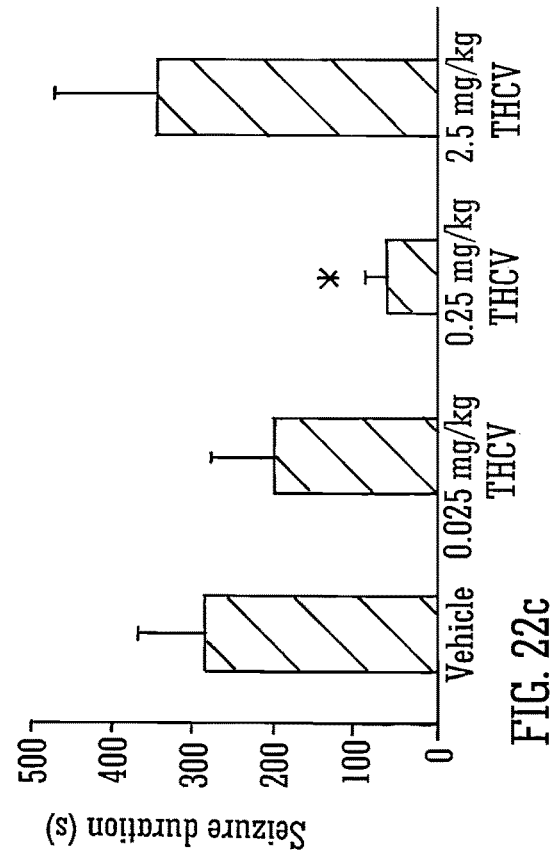
FIG. 22A-D show PTZ-induced seizure development and duration with isolated THCV.
Figure 22B:
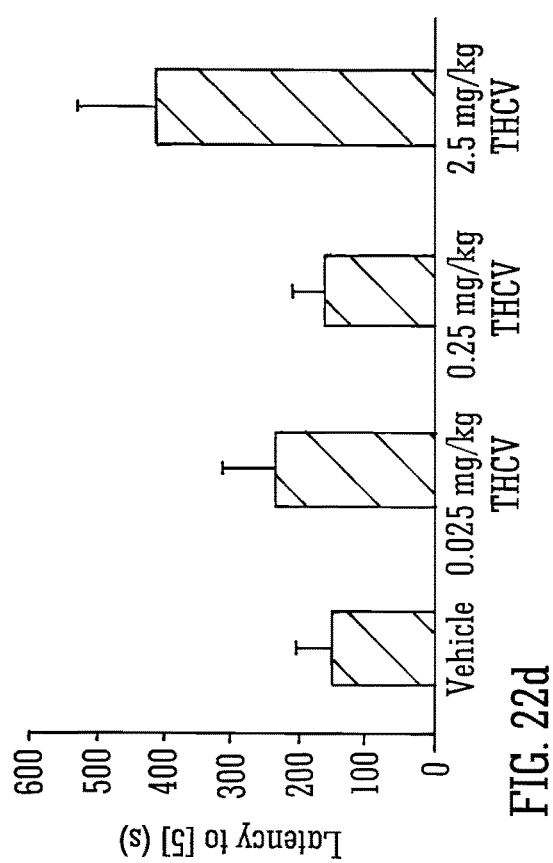
Figure 22C:
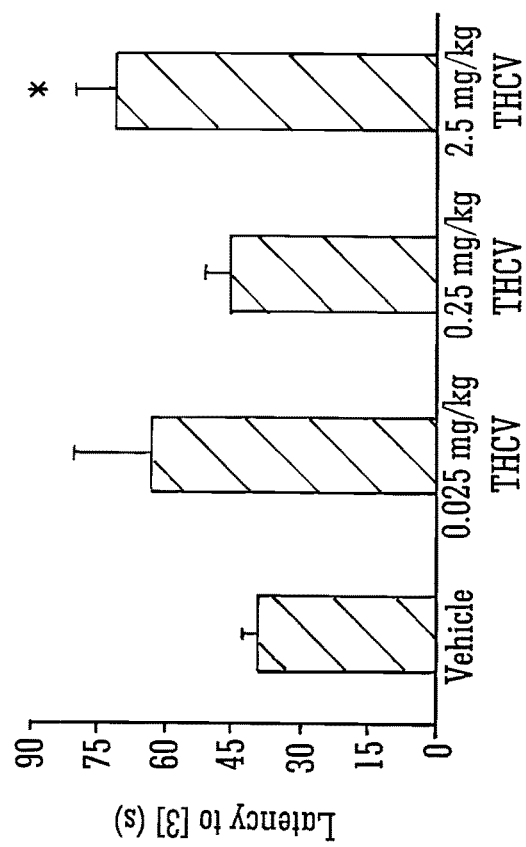
Figure 22D:
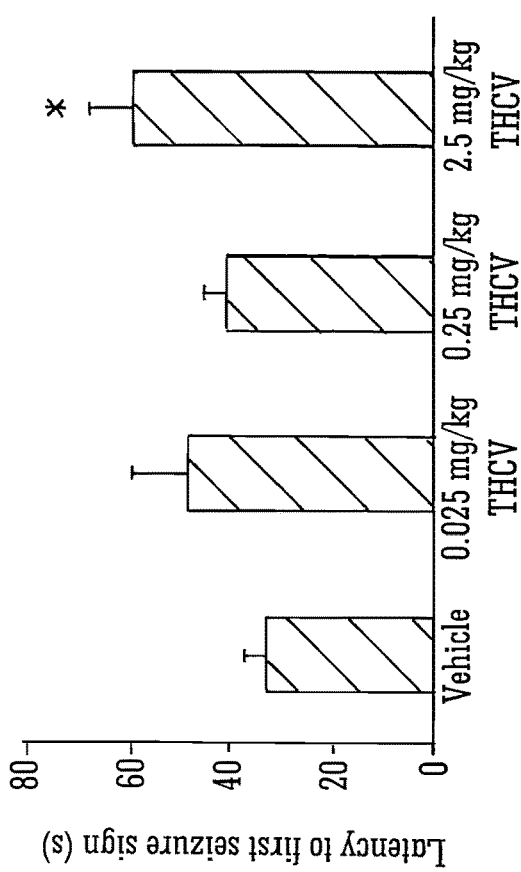

It was also observed that duration of PTZ-induced seizures in animals that survived the experimental period were significantly shorter after administration of the medium dose of THCV compared to vehicle controls (FIG. 22D; p=0.03). Table 8.2 below displays the values for median seizure severity in each experimental group.

TABLE 8.2

Seizure severity and incidence

|  | Vehicle | 0.025 mg/kg THCV | 0.25 mg/kg THCV | 2.5 mg/kg THCV |
|---|---|---|---|---|
| Median severity | 4.25 | 3.5 | 3.5 | 3.5 |
| % no seizure | 12.5 | 5.9 | 33.3* | 18.8 |

The median maximum severities and % of animals that did not experience any signs of seizure for each experimental group are given (n=16 for each value). * indicates significant difference from vehicle group (binomial significance test, P<0.05).

Vehicle control animals exhibited a median seizure severity of 4.25, whereas all groups which received THCV had a median severity score of 3.5. This decrease was not significantly different.

12.5% vehicle control animals displayed no indicators of seizure, suggesting these animals did not develop seizures after PTZ administration. A significantly higher number of animals (33.3%) displayed no signs of seizure in the group that received 0.25 mg/kg (Table 5.2; p=0.031). This data suggests that the medium dose of 0.25 mg/kg THCV protected against the development of seizures.

In Vivo Summary and Conclusion

The effects of the high dose of THCV on latency values suggest that THCV can delay both onset and seizure development, whilst the significant effects of the medium dose on the incidence of seizure at medium (0.25 mg/kg) THCV doses suggest a significant anticonvulsive action on PTZ-induced seizures.

Isolated CBD

In addition to THCV, CBD was also screened in the PTZ model. The results strongly indicate that CBD (at levels of 100 mg/kg) in this model is anti-convulsant as it significantly decreased the mortality rate and incidence of the most severe seizures compared to vehicle control animals.

Effect of Isolated CBD Against PTZ-Induced Seizures

Isolated CBD was injected intra-peritoneally (IP) in the standard vehicle (1:1:18 ethanol: Cremophor: 0.9% w/v NaCl) at doses of 1, 10 and 100 mg/kg alongside animals that received vehicle alone at a matched volume (n=15 for each group). 60 minutes later PTZ (80 mg/kg, IP) was administered.

46.7% of control animals that received vehicle alone died within 30 minutes of PTZ administration (FIG. 20). In contrast only 6.7% (only 1 of 15) of animals that received 100 mg/kg CBD died, a marked reduction that proved to be significant (p<0.001).

Additionally only 6.7% of animals that received 100 mg/kg CBD experienced the most severe seizures (score of 5) in comparison to 53.3% of vehicle control animals, a decrease that was also significant (p<0.001; FIG. 20 in vivo).

In contrast to isolated THCV, no significant increases in latency of seizure development were observed. However, the marked and significant reductions indicate a striking anti-convulsant effect on PTZ-induced seizures.

In Vivo Summary and Conclusion

Screening and analysis of isolated CBD in the PTZ model at high dose (100 mg/kg) of CBD on mortality levels and incidence of the most severe seizures suggests that CBD can attenuate the severity of PTZ-induced seizures.

Overall Conclusion

From the three studies it would appear that both isolated THCV and CBD show promise as an anti-epileptic for generalized seizure, particularly clonic/tonic seizure. The data generated for a THCV rich extract, containing other cannabinoids including significant amounts of THC, suggest that the THC may be countering the effect of the THCV and that a cannabinoid extract which contains THCV as a major or predominant cannabinoid, but which also contains minimal, or substantially no, THC would be desirable for treating epilepsy. Furthermore the results with pure CBD suggest that an extract containing significant amounts of both THCV and CBD, but again, minimal or substantially no THC may provide an optimum combination. Accordingly it may prove desirable to prepare a THCV predominant extract in which THC is selectively, and substantially, removed (to levels of less than a few percent). This could be mixed with a CBD rich extract in which CBD is the major and predominant cannabinoid (also with low levels of THC) to produce an extract with clearly defined, and significant levels of both THCV and CBD, but with insignificant levels of THC. Such an extract may contain other cannabinoids and the non-cannabinoid components which result from extraction, by for example, carbon dioxide as disclosed in WO04/016277, which components may support an "entourage" effect in the endocannabinoid system.

On dosage, a rat/human conversion factor ($\times 6$) suggests a CBD daily dose of at least 600 mg (and optionally between 400 mg and 800 mg) and for THCV at least 1.5 mg (medium) and preferably at least 15 mg (high).

Where a phytocannabinoid extract is to be used, an extract with low or negligible levels of THC and therapeutically effective levels of THCV and/or CBD is desired.

EXAMPLE 10

Comparison Between the Anti-Epileptic Activity of Isolated CBD and CBDV in the Maximal Electroshock Seizure (MES) Model of Epilepsy Methods Preparation of Test and Reference Compounds The vehicle used in this study was 2:1:17 (ethanol: Cremophor:0.9% $^w/_v$, NaCl). The test compounds used were cannabidiol (CBD) and cannabidivarin (CBDV). These were made to a solution at the highest concentration; these were then dissolved in ethanol before combination with Cremophor and 0.9% NaCl in the proportion described above. The CBD or CBDV were administered intraperitoneally at a volume of 10 ml/kg body weight. The SAED valproic acid (VBA) was dissolved in saline.

Test System

Animal Species/Strain: Mouse/ICR, Microbiological grade: SPF, Supplier: SLC Japan, Inc. Sex: male, Age (at time of testing): 5-7 weeks old, Number of animals: about 5 animals per group. Temperature: 23±2° C., Humidity: 60±10%, Light conditions: 7 AM to 7 PM for the light period, 7 PM to 7 AM for the dark period. Chow and water: Free access to CRF-1 (Oriental Yeast Co, Ltd) and tap water.

Experimental Procedures

One day before each experiment, mice were weighed and randomized into several groups in each test. On the morning of the experiment day, body weight was measured in order to calculate the administration volume of each animal.

Vehicle, CBD, CBDV or valproic acid sodium salt was interperitoneally administered 30 minutes before electric stimuli. Maximal electroshock seizures (MES) in mice was induced by a stimulator (UGO BASILE ECT UNIT 7801, Italia) using a current of 30 mA delivered with a pulse frequency of 100 Hz for 200 msec through earlap electrodes. The mice were observed for 10 seconds and the incidence of tonic hindlimb extension was noted.

Statistical Analysis

All statistical analyses were performed using SAS Software for Windows, Release 9.1 (SAS Institute Japan). The difference of the number (hindlimb extension or deaths) in each group was assessed using two-tailed Fisher's exact test. The differences were considered statistically significant, when the p value will be less than 0.05.

Results

Almost animals in the vehicle group showed a hindlimb extension induced by electric stimuli (30 mA for 200 msec). CBD (3-100 mg·kg IP) was not able to inhibit the expression of hindlimb extension with statistical significance. However CBDV (100 and 200 mg/kg IP) significantly inhibited the expression of hindlimb extension. Meanwhile, the 350 mg/kg of valproic acid blocked the hindlimb extension with statistical significance compared with vehicle group. Tables 10.1 and 10.2 detail these data.

TABLE 10.1

Effects of CBD and VPA on MES-induced seizure in mice

| Compound (Dose; mg/kg, i.p.) | Incidence of Tonic convulsion |
|---|---|
| Vehicle | 5/5 |
| CBD (3) | 3/5 |
| CBD (10) | 4/5 |
| CBD (30) | 3/5 |
| CBD (100) | 4/5 |
| Valproic acid (350) | 0/5** |

Each group consisted of 5 mice.
* = p < 0.05.
** = p < 0.01 vs vehicle control (Fisher's exact test)

TABLE 10.2

Effects of CBDV and VPA on MES-induced seizure in mice

| Compound (Dose; mg/kg, i.p.) | Incidence of Tonic convulsion |
|---|---|
| Vehicle | 9/10 |
| CBDV (50) | 9/10 |
| CBDV (100) | 3/10* |
| CBDV (200) | 3/10* |
| Valproic acid (200) | 5/10 |
| Valproic acid (350) | 1/10** |

Each group consisted of 10 mice.
* = p < 0.05.
** = p < 0.01 vs vehicle control (Fisher's exact test)

As can be seen from the data above the cannabinoid CBDV unexpectedly demonstrates greater efficacy as an anti-convulsant in the MES model of epilepsy than the cannabinoid CBD. Given that the efficacy of CBDV is approaching that of the SAED valproic acid it is a clear contender for use an anti-convulsant without producing the side effects that are known to occur with SAEDs.

EXAMPLE 11

The Effect of CBDV upon Motor Function Assessed by Linearly Accelerating Rotarod Test Methods Each animal received either CBDV (100 or 200 mg/kg, n=10 for each group) or vehicle (2:1:17 Cremophor:ethanol:saline [n=12] or saline [n=11]) on a given experimental day. Experimental test days were separated by a two day rest period to allow for clearance of previous compounds. The order of drug administration was randomised using a standard Latin square design.

60 minutes after CBDV or vehicle administration, animals were placed on a linearly accelerating rotarod (Panlab/Harvard Apparatus, Holliston, USA) that increased in speed from 4 to 40 rpm over a 300 second period. An accelerating protocol was employed to eliminate the need for habituation to the rotarod, minimising divergence in the results obtained for each animal owing to disproportionate improvements in performance. Each test ended when the animal fell from the rotarod, with each animal performing three accelerating rotarod runs per experimental day. Animals were allowed a 5 minute recovery between tests to prevent fatigue-induced declines in performance. Mean latency in seconds to fall from the rotarod was compared between vehicle control and CBDV groups to assess motor function.

To assess whether there were significant effects on motor function between the two different vehicle treatments, we subjected the data to Mann-Whitney U test. Lack of significance in this analysis would allow us to combine vehicle groups thereby reducing duration of testing (i.e. each rat would undertake only one vehicle treatment test day rather than two). For analysis of CBDV effects on motor function, data were subjected to a between-subjects 1-way ANOVA with drug concentration as the main factor. In all cases, $P \leq 0.05$ was considered to be significant.

Results

Analysis of Vehicle Treatments: As can be seen in FIG. 24, there was no difference in the latency to fall between saline and 2:1:17 cremaphor:ethanol:saline treated animals (P=0.406). Thus, both vehicle groups were combined to give us a single vehicle group Analysis of CBDV effects: As can be seen in FIG. 25, CBDV had no effect on the latency to fall compared to vehicle-dosed animals at any dose (F2, 40=1.421, P=0.253;). Vehicle treated animals remained on the rotarod for an average of 111.6 seconds, compared to 86.6 seconds at 100 mg/kg CBDV and 110.0 seconds at 200 mg/kg.

Conclusion

These data show that CBDV (100 and 200 mg/kg) had no significant effect on motor control or performance as assessed by accelerating rotarod. The rotarod tests the effect of drugs on the motor behaviour of the rats. Anti-convulsant drugs such as phenobarbital are known to produce a decrease in time that the animals can remain on the rotarod demonstrating the known side effects of these drugs on motor control.

Thus, the anti-convulsant effects demonstrated in the Examples above, in both the pentylenetetrazole model of generalised seizures and the pilocarpine model of temporal lobe seizures, are due to the phytocannabinoid CBDV controlling the seizure state without motor side-effects.

REFERENCES

ALGER, B. E. (2006) Not too excited? Thank your endocannabinoids. *Neuron,* 51, 393-5.

AMES FR. (1986) Anticonvulsant effect of cannabidiol. *South African Medical Journal* 69:14.

AVOLI, M., LOUVEL, J., PUMAIN, R. & KOHLING, R. (2005) Cellular and molecular mechanisms of epilepsy in the human brain. *Prog Neurobiol.*

BOSTANCI, M. O. & BAGIRICI, F. (2006) The effects of octanol on penicillin induced epileptiform activity in rats: an in vivo study. *Epilepsy Res,* 71, 188-94.

BRUST, J. C., NG, S. K., HAUSER, A. W. & SUSSER, M. (1992) Marijuana use and the risk of new onset seizures. *Trans Am Clin Climatol Assoc,* 103, 176-81.

CONSROE, P. F., WOOD, G. C. & BUCHSBAUM, H. (1975) Anticonvulsant Nature of Marihuana Smoking. *J. American Medical Association* 234 306-307

CUNHA, J. M., CARLINI, E. A., PEREIRA, A. E., RAMOS, O. L., PIMENTEL, C., GAGLIARDI, R., SANVITO, W. L., LANDER, N. & MECHOULAM, R. (1980) Chronic administration of cannabidiol to healthy volunteers and epileptic patients. *Pharmacology,* 21, 175-85.

DAVIS, M. I., RONESI, J. & LOVINGER, D. M. (2003) A Predominant Role for Inhibition of the Adenylate Cyclase/Protein Kinase A Pathway in ERK Activation by Cannabinoid Receptor 1 in N1E-115 Neuroblastoma Cells. *J. Biol. Chem.,* 278, 48973-48980.

DREIFUSS, F. E., BANCAUD, J., HENRIKSEN, O., RUBIO-DONNADIEU, F. PENRY, J. K. & SEINO, M. (1981) Proposal for revised clinical and electroencephalographic classification of epileptic seizures. *Epilepsia,* 22, 489-501.

FERDINAND, R. F., VAN DER ENDE, J., BONGERS, I., SELTEN, J. P., HUIZINK, A. & VERHULST, F. C. (2005) *Cannabis*-psychosis pathway independent of other types of psychopathology. *Schizophr Res,* 79, 289-95.

FISHER, R. S., VICKREY, B. G., GIBSON, P., HERMANN, B., PENOVICH, P., SCHERER, A. & WALKER, S. (2000) The impact of epilepsy from the patient's perspective I. Descriptions and subjective perceptions. *Epilepsy Res,* 41, 39-51.

GASTAUT, H. (1970) Clinical and Electroencephalographical Classification of Epileptic Seizures. *Epilepsia,* 11, 102-112.

LUTZ, B. (2004) On-demand activation of the endocannabinoid system in the control of neuronal excitability and epileptiform seizures. *Biochem Pharmacol,* 68, 1691-8.

MACKIE, K. (2006) Cannabinoid receptors as therapeutic targets. *Annu Rev Pharmacol Toxicol,* 46, 101-22.

MCCORMICK, D. A. & CONTRERAS, D. (2001) On the cellular and network bases of epileptic seizures. *Annu Rev Physiol,* 63, 815-46.

MERLIS, J. K. (1970) Proposal for an International Classification of the Epilepsies. *Epilepsia,* 11, 114-119.

N G et al. (1990) Illicit drug use and the risk of new-onset seizures, *American Journal of Epidemiology* 132: 47-57.

OBAY, B. D., TASDEMIR, E., TUMER, C., BILGIN, H. M. & SERMET, A. (2007) Antiepileptic effects of ghrelin on pentylenetetrazole-induced seizures in rats. *Peptides,* 28, 1214-9.

PEREIRA, M. B., FREITAS, R. L., ASSIS, M. A., SILVA, R. F., FONTELES, M. M., FREITAS, R. M. & TAKAHASHI, R. N. (2007) Study pharmacologic of the GABAergic and glutamatergic drugs on seizures and status epilepticus induced by pilocarpine in adult Wistar rats. *Neurosci Lett,* 419, 253-7.

PERTWEE R. G., (2000) Cannabinoid receptor ligands: clinical and neuropharmacological considerations, relevant to future drug discovery and development. *Exp. Opin. Invest. Drugs* 9(7):

RAUCA, C., WISWEDEL, I., ZERBE, R., KEILHOFF, G. & KRUG, M. (2004) The role of superoxide dismutase and alpha-tocopherol in the development of seizures and kindling induced by pentylenetetrazol-influence of the radical scavenger alpha-phenyl-N-tert-butyl nitrone. *Brain Res,* 1009, 203-12.

SANDER, J. W. (2003) The epidemiology of epilepsy revisited. *Curr Opin Neurol,* 16, 165-70.

SWANN, J. W. (2004) The effects of seizures on the connectivity and circuitry of the developing brain. *Ment Retard Dev Disabil Res Rev,* 10, 96-100.

TREMBLY B. SHERMAN M. (1990) Double-blind clinical study of cannabidiol as a secondary anticonvulsant. *Marijuana '90 International Conference on Cannabis and Cannabinoids. Kolympari, Crete, Jul.* 8-11, 1990.

WINGERCHUK, D. (2004) *Cannabis* for medical purposes: cultivating science, weeding out the fiction. *Lancet,* 364, 315-6.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety, particularly for the disclosure referenced herein.

The invention claimed is:

1. A method for the treatment of partial seizures, which comprises administering to a subject in need thereof a therapeutically effective amount of the phytocannabinoid CBDV, wherein the CBDV is present as the only active cannabinoid.

2. The method of claim 1, wherein the partial seizure to be treated is a temporal lobe seizure.

3. The method of claim 1, wherein the CBDV is used in combination with a standard anti-epileptic drug.

4. The method of claim 3, wherein the standard antiepileptic drug is phenobarbital.

5. The method of claim 3, wherein the standard antiepileptic drug is ethosuximide.

6. The method of claim 3, wherein the standard antiepileptic drug is valproate.

* * * * *